(12) United States Patent
Shpak et al.

(10) Patent No.: US 12,268,549 B2
(45) Date of Patent: *Apr. 8, 2025

(54) METHOD AND SYSTEM FOR PERFORMING TIME-DOMAIN PROCESSING OF A WAVEFORM SIGNAL

(71) Applicant: SPARROW ACOUSTICS INC., Lucasville (CA)

(72) Inventors: Yaroslav Shpak, Kiev (UA); Maksim Davydov, Fanipol (BY)

(73) Assignee: SPARROW ACOUSTICS INC., Lucasville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,252

(22) Filed: Dec. 13, 2023

(65) Prior Publication Data

US 2024/0108305 A1   Apr. 4, 2024

Related U.S. Application Data

(63) Continuation of application No. 18/086,050, filed on Dec. 21, 2022, now Pat. No. 11,877,884, which is a
(Continued)

(51) Int. Cl.
*A61B 7/04* (2006.01)
*G01N 29/42* (2006.01)

(52) U.S. Cl.
CPC ............... *A61B 7/04* (2013.01); *G01N 29/42* (2013.01)

(58) Field of Classification Search
CPC .................................. A61B 7/04; G01N 29/42
See application file for complete search history.

(56) References Cited

U.S. PATENT DOCUMENTS 4,094,304 A * 6/1978 Wright, Jr. ............ G01V 1/306
                                                          600/552
4,792,145 A   12/1988 Eisenberg et al.
(Continued)

FOREIGN PATENT DOCUMENTS

CN        1230278 A  *  9/1999  ......... G02B 26/0833
CN      102125442 A       7/2011
(Continued)

OTHER PUBLICATIONS

Steth IO User's Guide, Document No. 11-00-UM-1000-00, Revision E, Oct. 12, 2018, 19 pages.
(Continued)

*Primary Examiner* — Michael J Dalbo
*Assistant Examiner* — Kaleria Knox
(74) *Attorney, Agent, or Firm* — BCF LLP

(57) ABSTRACT

Method and processor for time-domain processing of a waveform signal are disclosed. The method includes filtering, by employing one or more cut-off frequency values, the waveform signal for generating the first portion and the second portion, acquiring a frequency shift value, generating a modulated signal having a first frequency portion and a second frequency portion and where the one or more cut-off frequency values have been determined for ensuring that the first frequency portion and the second frequency portion are non-overlapping portions of the modulated signal, and generating the modified signal using the first frequency portion.

20 Claims, 19 Drawing Sheets

Related U.S. Application Data continuation of application No. PCT/CA2021/051232, filed on Sep. 7, 2021.

(60) Provisional application No. 63/076,071, filed on Sep. 9, 2020.

(56) References Cited

U.S. PATENT DOCUMENTS

| | | | |
|---|---|---|---|
| 6,873,955 B1 * | 3/2005 | Suzuki | G10H 1/0041 |
| | | | 704/238 |
| 8,200,277 B2 | 6/2012 | Lee | |
| 9,445,763 B2 | 9/2016 | Davis et al. | |
| 9,485,345 B2 | 11/2016 | Chandrasekaran et al. | |
| 9,610,042 B1 | 4/2017 | Vyshedskiy | |
| 9,814,438 B2 | 11/2017 | Stamatopoulos et al. | |
| 9,820,696 B1 | 11/2017 | Narasimhan | |
| 9,848,848 B2 | 12/2017 | Emmanouilidou et al. | |
| 9,866,953 B2 | 1/2018 | Chong et al. | |
| 10,004,473 B2 | 6/2018 | Tsai et al. | |
| 10,098,569 B2 | 10/2018 | Abeyratne et al. | |
| 10,229,754 B2 | 3/2019 | Cronin et al. | |
| 10,993,670 B2 | 5/2021 | Shute et al. | |
| 2005/0078533 A1 | 4/2005 | Vyshedskiy et al. | |
| 2014/0371631 A1 | 12/2014 | Fontana | |
| 2016/0224312 A1 | 8/2016 | Wu | |
| 2016/0302003 A1 | 10/2016 | Rahman et al. | |
| 2017/0112439 A1 | 4/2017 | Dubin | |
| 2017/0233536 A1 | 8/2017 | Siripurapu | |
| 2018/0228468 A1 * | 8/2018 | Adler | A61B 8/5223 |
| 2019/0059824 A1 | 2/2019 | Chen et al. | |
| 2019/0109684 A1 * | 4/2019 | Chen | H04L 5/003 |
| 2021/0235203 A1 | 7/2021 | Lunner | |

FOREIGN PATENT DOCUMENTS

| | | | | |
|---|---|---|---|---|
| CN | 201977775 U | 9/2011 | | |
| CN | 202026360 U | 11/2011 | | |
| CN | 102512138 A | 6/2012 | | |
| CN | 103340650 A | 10/2013 | | |
| CN | 203408062 U | 1/2014 | | |
| CN | 102685285 B | 8/2016 | | |
| CN | 109589129 A | 4/2019 | | |
| EP | 3416564 B1 | 6/2020 | | |
| JP | 2012512437 A * | 5/2012 | | |
| JP | 2013146287 A | 8/2013 | | |
| WO | 2011013881 A1 | 2/2011 | | |
| WO | 2013152022 A1 | 10/2013 | | |
| WO | WO-20130152022 A1 * | 10/2013 | | H04L 7/00 |
| WO | WO-2017075601 A1 * | 5/2017 | | A61B 5/08 |
| WO | 2021054742 A1 | 3/2021 | | |

OTHER PUBLICATIONS

3M Littmann Brand, Electronic Stethoscope Model 3200 User Manual, 2009, 16 pages.

Supplementary European Search Report issued in corresponding European patent application No. 21865417.6 on Aug. 9, 2024.

Non-Final Rejection issued in U.S. Appl. No. 18/482,387 on Nov. 7, 2024.

* cited by examiner

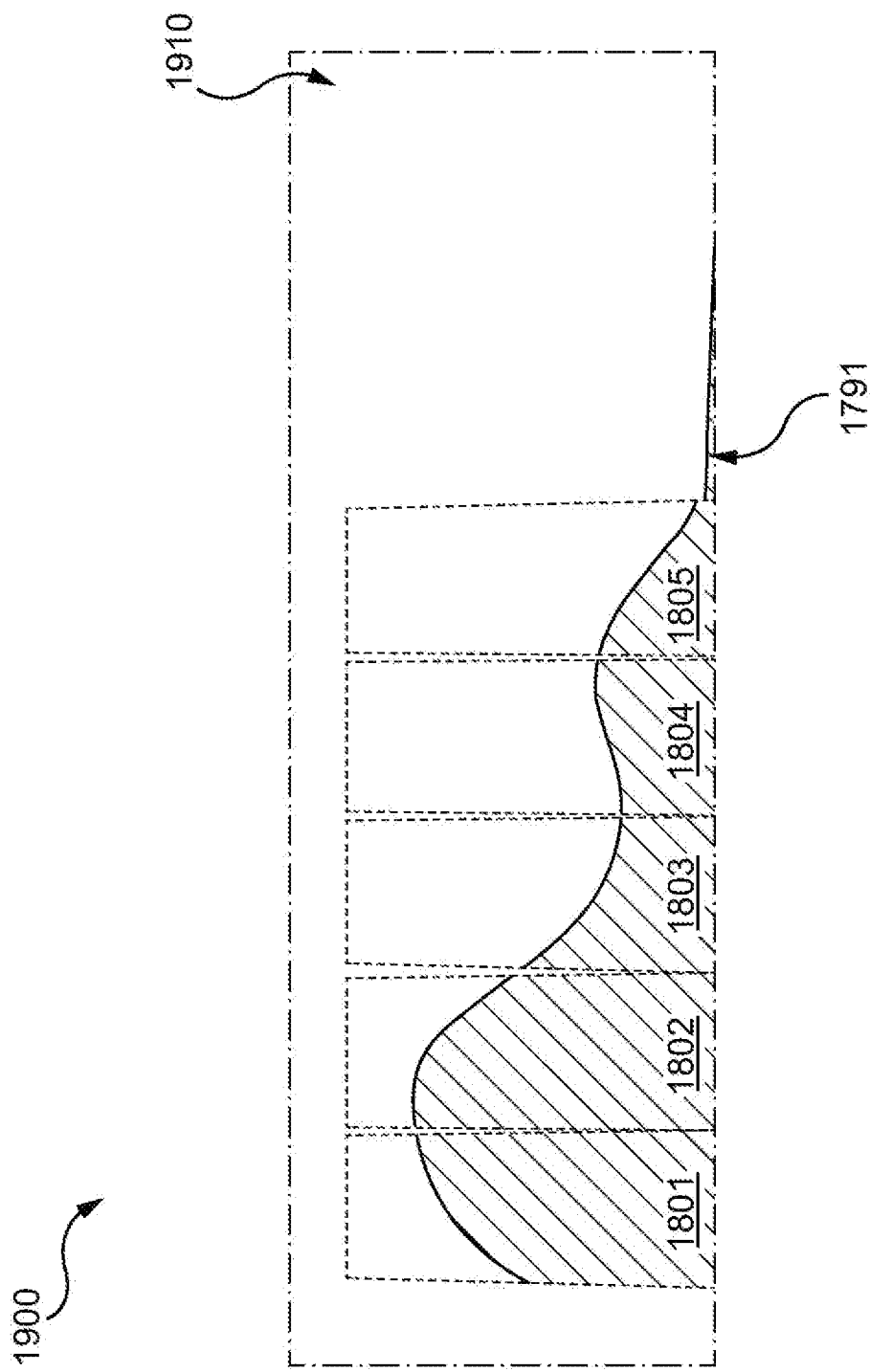

METHOD AND SYSTEM FOR PERFORMING TIME-DOMAIN PROCESSING OF A WAVEFORM SIGNAL

CROSS-REFERENCE TO RELATED APPLICATIONS

This application is a Continuation of U.S. patent application Ser. No. 18/086,050 filed on Dec. 21, 2022, which is a Continuation of international PCT patent application No. PCT/CA2021/051232 filed on Sep. 7, 2021, which claims the benefit of priority of U.S. provisional application No. 63/076,071 filed on Sep. 9, 2020. The contents of the above noted applications are incorporated herein by reference in their entirety.

FIELD

The present technology relates to sound processing in general, and specifically to methods and systems for performing time-domain processing of a waveform signal.

BACKGROUND

Auscultation has been a key technique in medical diagnosis for centuries. In auscultation, a medical practitioner listens to the internal sounds of the body, typically using a stethoscope. For example, a stethoscope can be used for listening to internal sounds from the heart, lungs, and other organs.

Auscultation is most commonly performed for the purpose of examining the circulatory and respiratory systems, and thus diagnosing conditions of the heart and lungs in particular. In more recent years, electronic stethoscopes and methods of digital processing of body sounds have become available, in order to enhance and supplement the medical practitioner's auditory capabilities.

For example, U.S. Patent Application Publication US 2018/0228468 describes methods for processing an electrical signal so as to generate a frequency-stretched signal in which infrasonic frequency components of the electrical input are shifted to audible frequencies. This processing for generating of a frequency-stretched signal is performed in frequency-domain.

SUMMARY

It is an object of the present technology to ameliorate at least some of the inconveniences present in the prior art. Embodiments of the present technology may provide and/or broaden the scope of approaches to and/or methods of achieving the aims and objects of the present technology.

Conventional electronic stethoscopes need to process sound data in order to enhance or supplement a medical practitioner's auditory capabilities. However, processing of sound data may introduce a considerable amount of noise into the audio signal which is detrimental to the medical practitioner's ability to recognize potential issues with the patient's organs.

In at least some non-limiting embodiments of the present technology, the developers of the present technology have devised methods and devices for generating an augmented audio signal having a first portion (in some cases, a non-audible portion) of the original signal, containing relevant information for diagnosis, which has been "shifted" to higher (e.g., audible) frequencies. Although some conventional electronic stethoscopes are able to shift a portion of the original audio signal, sound processing for that purpose is performed in the frequency-domain which can introduce a considerable amount of noise into the final audio signal, which is detrimental for the ability of the medical practitioner to fully appreciate the information from the final audio signal.

As it will become apparent from the description herein further below, one or more computer-implemented sound filtering procedures may be used in the context of the present technology for processing sound data in the time-domain Developers of the present technology have realized that using computer-implemented sound filtering procedures may be less expensive to implement than mechanically-implemented filtering solutions. It is further contemplated that using computer-implemented sound filtering procedures, further allows processing the sound data on any electronic device suitable for running these computer-implemented sound filtering procedures, as opposed to requiring one or more mechanical filters of a particular electronic device.

It is contemplated that one or more filters employed in at least some embodiments of the present technology may comprise a finite impulse response digital filter, an infinite impulse response digital filter, a Chebyshev digital filter, a Butterworth digital filter, and the like.

In a first broad aspect of the present technology, there is provided a method of time-domain processing of a waveform signal for generating a modified waveform signal. The waveform signal is representative of bodily sounds. The method is executable by an electronic device that has a processor. The waveform signal is available to the processor. The method comprises filtering, by the processor employing one or more cut-off frequency values, the waveform signal for generating a first portion of the waveform signal and a second portion of the waveform signal. The first portion is in a first frequency range, and the second portion is in a frequency range that is inside a human-audible frequency range. The method comprises acquiring, by the processor, a frequency shift value of a frequency range by which the first portion is to be shifted to frequencies above the first frequency range. The method comprises generating, by the processor, a modulated signal using the first portion and a modulation signal. The modulation signal has a frequency equal to the frequency shift value and a time-length equal to a time-length of the waveform signal. The modulated signal comprises a first frequency portion being in a frequency range that is above the frequency shift value and a second frequency portion being in a frequency range that is below the frequency shift value. The one or more cut-off frequency values have been determined so that the first frequency portion and the second frequency portion are in substantially non-overlapping frequency ranges of the modulated signal. The first frequency portion is a modified representation of the first portion of the waveform signal. The frequency range of the first frequency portion is inside the human-audible frequency range. The method comprises generating, by the processor, the modified waveform using the first frequency portion of the modulated signal.

In another aspect of the present technology, there is provided a method of time-domain processing of a waveform signal for generating a modified waveform signal. The waveform signal is representative of bodily sounds. The method is executable by an electronic device that has a processor. The waveform signal is available to the processor. The method comprises filtering, by the processor employing one or more cut-off frequency values, the waveform signal for generating a first portion of the waveform signal and a second portion of the waveform signal. The first portion is in a first frequency range, and the second portion is in a frequency range that is inside a human-audible frequency range. The method comprises acquiring, by the processor, a frequency shift value of a frequency range by which the first portion is to be shifted to frequencies above the first frequency range. The method comprises generating, by the processor, a modulated signal using the first portion and a modulation signal. The modulation signal has a frequency equal to the frequency shift value and a time-length equal to a time-length of the waveform signal. The modulated signal comprises a first frequency portion being in a frequency range that is above the frequency shift value and a second frequency portion being in a frequency range that is below the frequency shift value. The one or more cut-off frequency values have been determined so that the first frequency portion and the second frequency portion have no overlap in frequency ranges of the modulated signal or have an overlap of less than about 0.5%.

In some embodiments of the method, the method further comprises generating, by the processor, the modified waveform signal as a combination of the second portion of the waveform signal and the first frequency portion.

In some embodiments of the method, the one or more cut-off frequency values have been determined for ensuring that the first frequency portion and the second frequency portion are in non-overlapping frequency ranges of the modulated signal.

In some embodiments of the method, the first portion of the waveform signal is a non-audible portion and the second portion is an audible portion of the waveform signal. The non-audible portion is in a frequency range that is outside the human-audible frequency range.

In some embodiments of the method, the method further comprises determining, by the processor, the one or more cut-off frequency values based on an input from a human operator.

In some embodiments of the method, the filtering comprises filtering, by the processor employing a first and a second cut-off frequency values, the waveform signal for generating the first portion. The second cut-off frequency value depends on the frequency shift value. The second cut-off frequency value may be predetermined.

In some embodiments of the method, the method further comprises filtering, by the processor employing a third cut-off frequency value, the modulated signal for generating the first frequency portion. The third cut-off frequency value depends on the first cut-off frequency value and the frequency shift value.

In some embodiments of the method, the generating the modified signal comprises generating, by the processor, a normalized signal based on the first frequency portion, and generating, by the processor, the modified signal as a combination of the normalized signal and the second portion.

In some embodiments of the method, the filtering comprises filtering, by the processor employing a fourth cut-off frequency values, the waveform signal for generating the second portion. The fourth cut-off frequency value depends on the frequency shift value.

In some embodiments of the method, the frequency shift value is acquired from a memory associated with the electronic device.

In some embodiments of the method, the frequency shift value is acquired as an input of a human operator.

In some embodiments of the method, the method further comprises storing, by the processor in a memory, the modified waveform signal.

In some embodiments of the method, the method further comprises triggering, by the processor, generation of sound representative of the modified waveform signal for a human operator.

In some embodiments of the method, the electronic device is an electronic stethoscope.

In some embodiments of the method, the frequency shift value is 45 Hz.

In some embodiments of the method, the first cut-off frequency value is 5 Hz and the second cut-off frequency value is 90 Hz. The first cut-off frequency may be pre-determined.

In some embodiments of the method, the third cut-off frequency value is 50 Hz. The third cut-off frequency may be pre-determined.

In some embodiments of the method, the fourth cut-off frequency value is 135 Hz. The fourth cut-off frequency may be pre-determined.

In some embodiments of the method, the waveform signal comprises a plurality of first portions including the first portion. The generating the modulated signal comprises generating, by the processor, a plurality of modulated signals using the respective ones of the plurality of first portions and the modulated signal. The plurality of modulated signals comprising a plurality of first frequency portions. The generating the modified waveform signal comprises generating, by the processor, the modified waveform signal as a combination of the second portion of the waveform signal and the plurality of first frequency portions.

In certain embodiments, the method comprises determining presence or absence of a condition of the patient from the modulated signal using one or more predetermined condition factors. The predetermined condition factors may comprise a signal frequency range, a signal frequency threshold, a signal amplitude, and a signal pattern. The condition may be one or more of: coronary artery disease, valve disease, arrhythmia, peripheral vascular disease, congenital heart defects, hypertension, and cardiomyopathy, to name a few.

In a second broad aspect of the present technology, there is provided a processor for time-domain processing of a waveform signal for generating a modified waveform signal. The waveform signal is representative of bodily sounds. The waveform signal is available to the processor. The processor is configured to filter, by employing one or more cut-off frequency values, the waveform signal for generating a first portion of the waveform signal and a second portion of the waveform signal. The first portion is in a first frequency range, and the second portion is in a frequency range that is inside a human-audible frequency range. The processor is configured to acquire a frequency shift value indicative of a frequency range by which the first portion is to be shifted to frequencies above the first frequency range. The processor is configured to generate a modulated signal using the first portion and a modulation signal. The modulation signal has a frequency equal to the frequency shift value and a time-length equal to a time-length of the waveform signal. The modulated signal comprises a first frequency portion being in a frequency range that is above the frequency shift value and a second frequency portion being in a frequency range that is below the frequency shift value. The one or more cut-off frequency values have been determined so that the first frequency portion and the second frequency portion are in substantially non-overlapping frequency ranges of the modulated signal. The first frequency portion is a modified representation of the first portion of the waveform signal. The frequency range of the first frequency portion is inside the human-audible frequency range. The processor is configured to generate the modified waveform using the first frequency portion of the modulated signal.

In some embodiments of the processor, the processor is further configured to generate the modified waveform signal as a combination of the second portion of the waveform signal and the first frequency portion.

In some embodiments of the processor, the one or more cut-off frequency values have been determined for ensuring that the first frequency portion and the second frequency portion are in non-overlapping frequency ranges of the modulated signal.

In some embodiments of the processor, the first portion of the waveform signal is a non-audible portion and the second portion is an audible portion of the waveform signal. The non-audible portion being in a frequency range that is outside the human-audible frequency range.

In some embodiments of the processor, the processor is further configured to determine the one or more cut-off frequency values based on an input from a human operator.

In some embodiments of the processor, the processor configured to filter comprises the processor configured to filter, by employing a first and a second cut-off frequency values, the waveform signal for generating the first portion. The second cut-off frequency value depends on the frequency shift value.

In some embodiments of the processor, the processor is further configured to filter, by employing a third cut-off frequency value, the modulated signal for generating the first frequency portion. The third cut-off frequency value depends on the first cut-off frequency value and the frequency shift value.

In some embodiments of the processor, the processor configured to generate the modified signal comprises the processor configured to generate a normalized signal based on the first frequency portion and generate the modified signal as a combination of the normalized signal and the second portion.

In some embodiments of the processor, the processor configured to filter comprises the processor configured to filter, by employing a fourth cut-off frequency values, the waveform signal for generating the second portion. The fourth cut-off frequency value depends on the frequency shift value.

In some embodiments of the processor, the frequency shift value is acquired from a memory associated with the electronic device.

In some embodiments of the processor, the frequency shift value is acquired as an input of a human operator.

In some embodiments of the processor, the processor is further configured to store, in a memory, the modified waveform signal.

In some embodiments of the processor, the processor is further configured to trigger generation of sound representative of the modified waveform signal for a human operator.

In some embodiments of the processor, the electronic device is an electronic stethoscope.

In some embodiments of the processor, the frequency shift value is 45 Hz.

In some embodiments of the processor, the first cut-off frequency value is 5 Hz and the second cut-off frequency value is 90 Hz. The first cut-off frequency may be pre-determined.

In some embodiments of the processor, the third cut-off frequency value is 50 Hz. The third cut-off frequency may be pre-determined.

In some embodiments of the processor, the fourth cut-off frequency value is 135 Hz. The fourth cut-off frequency may be pre-determined.

In some embodiments of the present technology, the waveform signal comprises a plurality of first portions including the first portion. The processor configured to generate the modulated signal comprises the processor configured to generate a plurality of modulated signals using the respective ones of the plurality of first portions and the modulated signal. The plurality of modulated signals comprises a plurality of first frequency portions. The processor configured to generate the modified waveform signal comprises the processor configured to generate the modified waveform signal as a combination of the second portion of the waveform signal and the plurality of first frequency portions.

In the context of the present specification, "electronic device" is any computer hardware that is capable of running software appropriate to the relevant task at hand. Thus, some (non-limiting) examples of client devices include personal computers (desktops, laptops, netbooks, etc.), smartphones, and tablets, as well as network equipment such as routers, switches, and gateways. It should be noted that a device acting as a client device in the present context is not precluded from acting as a server to other client devices. The use of the expression "a client device" does not preclude multiple client devices being used in receiving/sending, carrying out or causing to be carried out any task or request, or the consequences of any task or request, or steps of any method described herein.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, the expression "component" is meant to include software (appropriate to a particular hardware context) that is both necessary and sufficient to achieve the specific function(s) being referenced.

In the context of the present specification, the expression "computer usable information storage medium" is intended to include media of any nature and kind whatsoever, including RAM, ROM, disks (CD-ROMs, DVDs, floppy disks, hard drivers, etc.), USB keys, solid state-drives, tape drives, etc.

In the context of the present specification, unless expressly provided otherwise, an "indication" of an information element may be the information element itself or a pointer, reference, link, or other indirect mechanism enabling the recipient of the indication to locate a network, memory, database, or other computer-readable medium location from which the information element may be retrieved. For example, an indication of a document could include the document itself (i.e. its contents), or it could be a unique document descriptor identifying a file with respect to a particular file system, or some other means of directing the recipient of the indication to a network location, memory address, database table, or other location where the file may be accessed. As one skilled in the art would recognize, the degree of precision required in such an indication depends on the extent of any prior understanding about the interpretation to be given to information being exchanged as between the sender and the recipient of the indication. For example, if it is understood prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first server" and "third server" is not intended to imply any particular order, type, chronology, hierarchy or ranking (for example) of/between the server, nor is their use (by itself) intended imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 19 depicts a representation of a frequency spectrum of a given modified waveform signal generated based on the given waveform signal of FIG. 17, in accordance with some non-limiting embodiments of the present technology.

DETAILED DESCRIPTION

Figure 1:
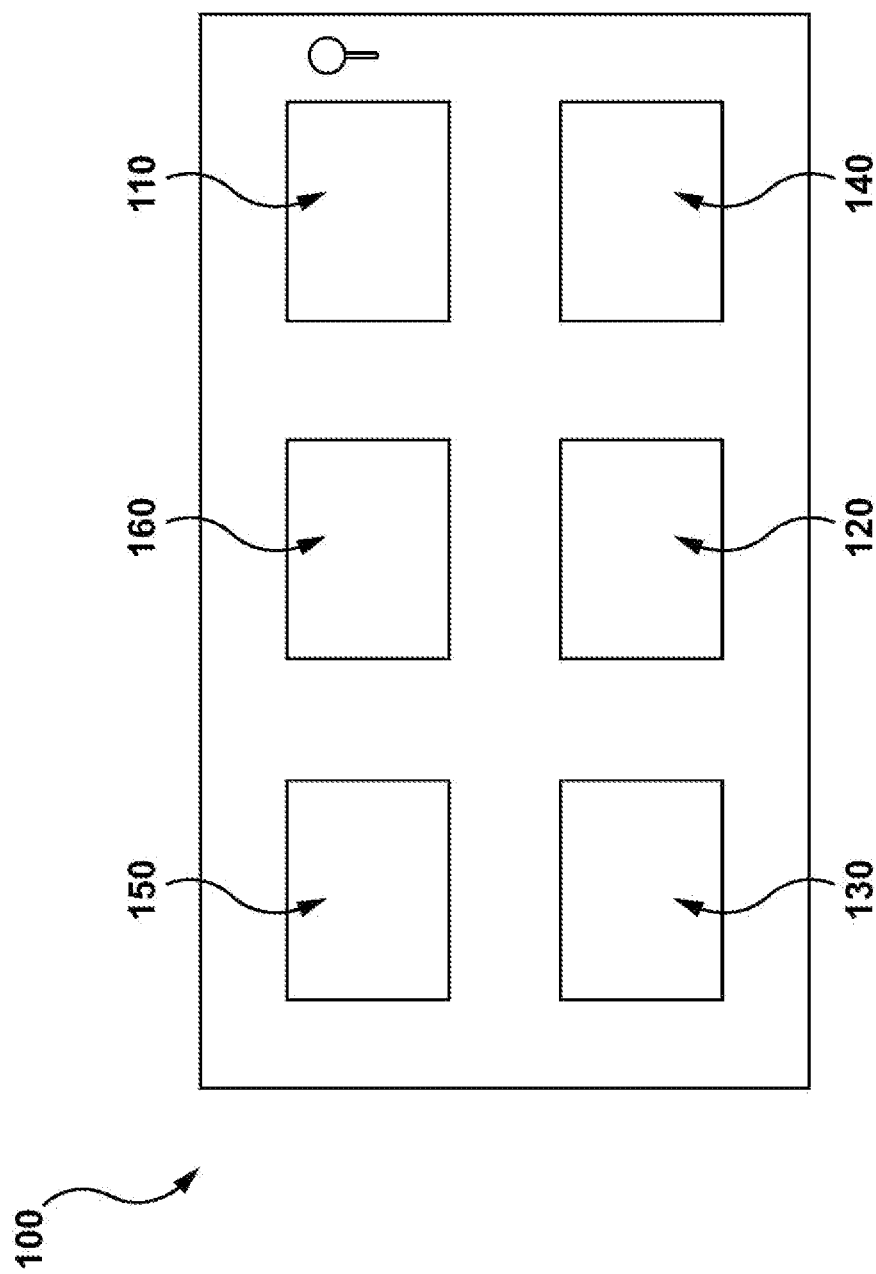
FIG. 1 depicts a computer system suitable for use with some non-limiting embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

Computer System

Referring initially to FIG. 1, there is depicted a computer system 100 suitable for use with some implementations of the present technology, the computer system 100 comprising various hardware components including one or more single or multi-core processors collectively represented by a processor 110, a solid-state drive 120, a memory 130, which may be a random-access memory or any other type of memory. Communication between the various components of the computer system 100 may be enabled by one or more internal and/or external buses (not shown) (e.g. a PCI bus, universal serial bus, IEEE 1394 "Firewire" bus, SCSI bus, Serial-ATA bus, etc.), to which the various hardware components are electronically coupled.

In at least some embodiments of the present technology, the solid-state drive 120 stores program instructions suitable for being loaded into the memory 130 and executed by the processor 110 for performing time-domain processing of sound data. For example, the program instructions may be part of a time-domain processing application executable by the processor 110.

In some non-limiting embodiments of the present technology, the computer system 100 comprises a sound-detecting component 150. For example, the sound-detecting component 150 may be implemented as one or more microphones configured to detect, and capture sound (e.g., bodily sounds of a given patient) in any suitable audio format. That is, the sound-detecting component 150 can be said to detect sound and generate a waveform signal representative of that sound for further use thereof. Also, the computer system 100 comprises a sound-reproducing component 160. For example, the sound-reproducing component 160 may be implemented as one or more speakers configured to acquire sound data and reproduce sound (e.g., to be heard by a medical practitioner). That is, the sound-reproducing component 160 can be said to receive a waveform signal and use it for generating an audible representation thereof to a given user.

In at least some embodiments of the present technology, it is contemplated that the computer system 100 may have additional and/or optional components, such as a network communication module 140 for communication, with other electronic devices and/or servers, localization modules (not depicted), and the like.

Figure 2:
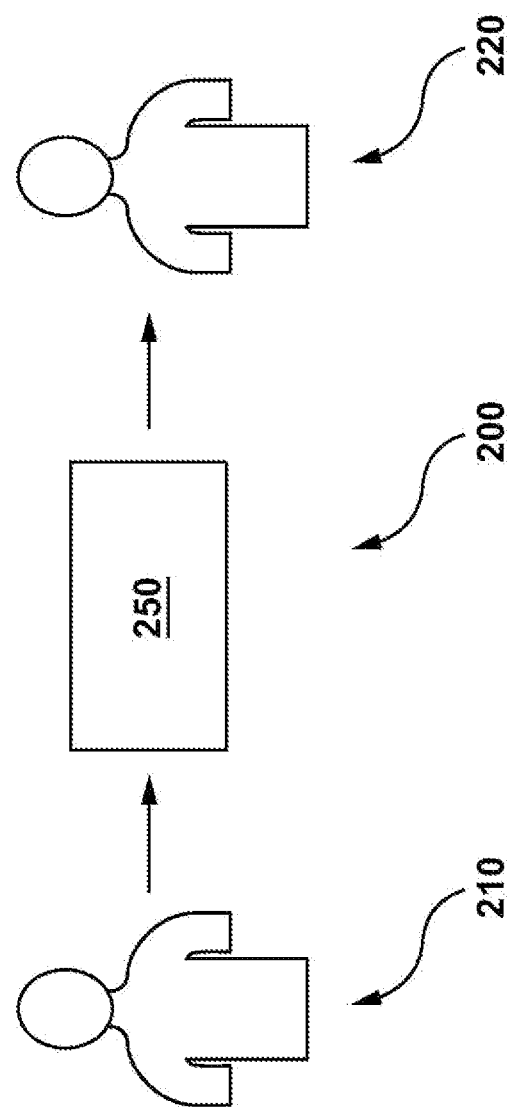
FIG. 2 depicts a representation of an electronic device for processing a waveform signal, in accordance with at least some non-limiting embodiments of the present technology.

With reference to FIG. 2, there is depicted a representation 200 of an electronic device 250 in accordance with at least some non-limiting embodiments of the present technology. How the electronic device 250 is implemented is not particularly limiting. However, just as an example, the electronic device 250 may comprise one or more components of the computer system 100 illustrated in FIG. 1.

In one non-limiting implementation of the present technology, the electronic device 250 may be implemented as an electronic stethoscope. Broadly speaking, a given electronic stethoscope is an electronic medical instrument for listening to the action of a user's heart or breathing. Typically, they include a computer system for inter alia sound data processing, a small disc-shaped resonator to be placed against the chest of a patient for capturing sound, and earpieces for reproducing sound to a user of the electronic stethoscope.

For example, as illustrated in FIG. 2, a medical practitioner 220 may use the electronic stethoscope to capture sound from a patient's 210 body, which then processes the sound, and provides an enhanced representation of that sound to the medical practitioner 220. It is contemplated that the medical practitioner 220 may be a human operator of the electronic device 250 (e.g., the electronic stethoscope).

Nevertheless, it should be noted that the electronic device 250 being a given electronic stethoscope is only one non-limiting implementation of the present technology. In other embodiments, the electronic device 250 may be implemented as any electronic device suitable for processing a waveform signal associated with the patient 210 for generating a modified waveform signal via execution of one or more computer-implemented procedures described herein.

For example, the electronic device 250 may also be implemented as a personal computer, a laptop, a server, a communication device, a wearable device, or the like, without departing from the scope of the present technology.

In at least some embodiments of the present technology, it is contemplated that the electronic device 250 may be implemented as an "off-the-shelf" smartphone device. For example, one or more sound processing techniques disclosed herein may be enabled through an application downloadable on the off-the-shelf smartphone device. In this example, the application may be downloadable from an "app store" and/or via any other suitable means without departing from the scope of the present technology. Hence, it can be said that a given processor configured to implement the one or more sound processing techniques disclosed herein may be a processor of the smartphone device.

Figure 3:
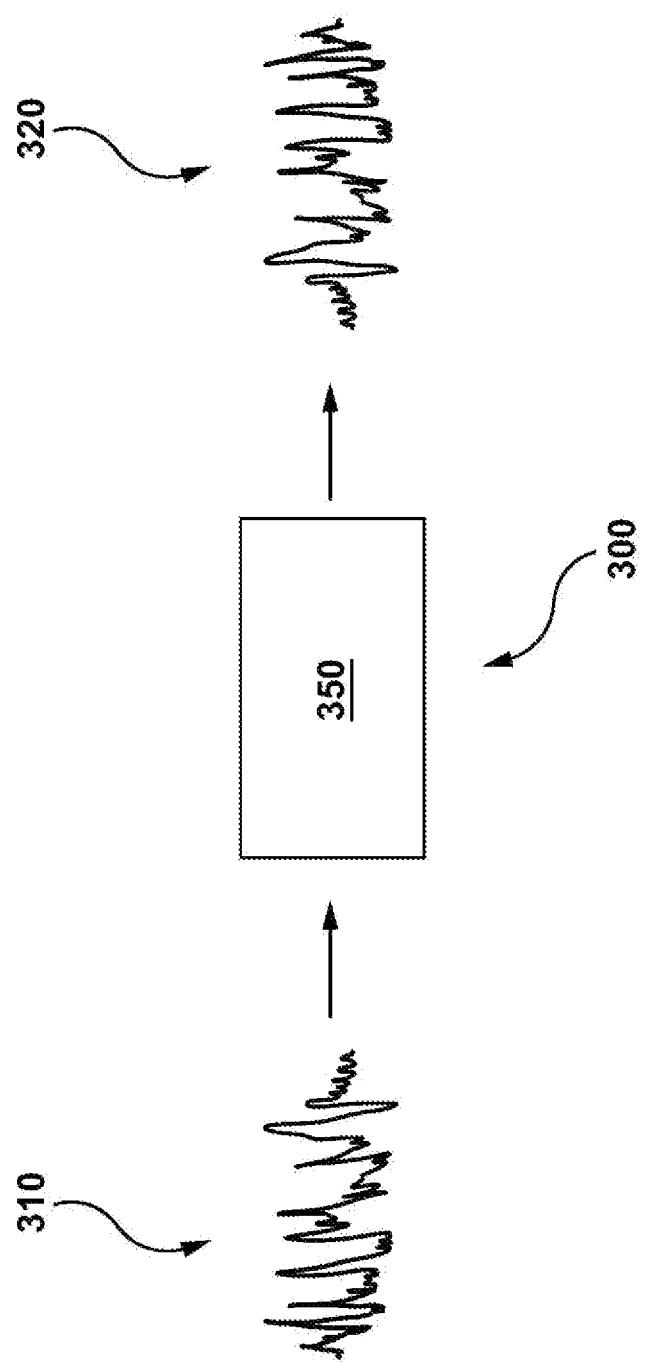
FIG. 3 depicts a representation of how the electronic device of FIG. 2 generates a modified waveform signal based on a respective waveform signal, in accordance with at least some non-limiting embodiments of the present technology.

With reference to FIG. 3, there is depicted a representation 300 of how the electronic device 250 of FIG. 2 generates a modified waveform signal 320 based on a respective waveform signal 310 associated with the patient 210. As illustrated and previously alluded to, the electronic device 250 is configured to execute a plurality of sound processing computer-implemented procedures 350 in order to process the waveform signal 310.

How the plurality of sound processing computer-implemented procedures 350 are executed by the electronic device 250, in some embodiments of the present technology, will be described in greater detail herein further below with reference to FIG. 5. However, it should be noted that the purpose of the plurality of sound processing computer-implemented procedures 350 is to generate the modified waveform signal 320 that can enhance and/or supplement auditory capabilities of the medical practitioner 220. In other embodiments, it is contemplated that the modified waveform signal 320 may allow the processor 110 to determine a condition, such as a health condition, of the patient. For example, the processor 110 may be configured to identify one or more sound or signal patterns indicative of a condition if compared to the waveform signal 310. For example, the processor 110 may be configured to apply one or more computer-implemented procedures for identifying a sound pattern in the modified signal 320 and which is indicative of an illness of the patient. In certain embodiments, the modified waveform signal 320 may be used to determine a presence or an absence of a condition. In certain embodiments, the condition may be one or more of: coronary artery disease, valve disease, arrhythmia, peripheral vascular disease, congenital heart defects, hypertension, and cardiomyopathy.

Figure 4:
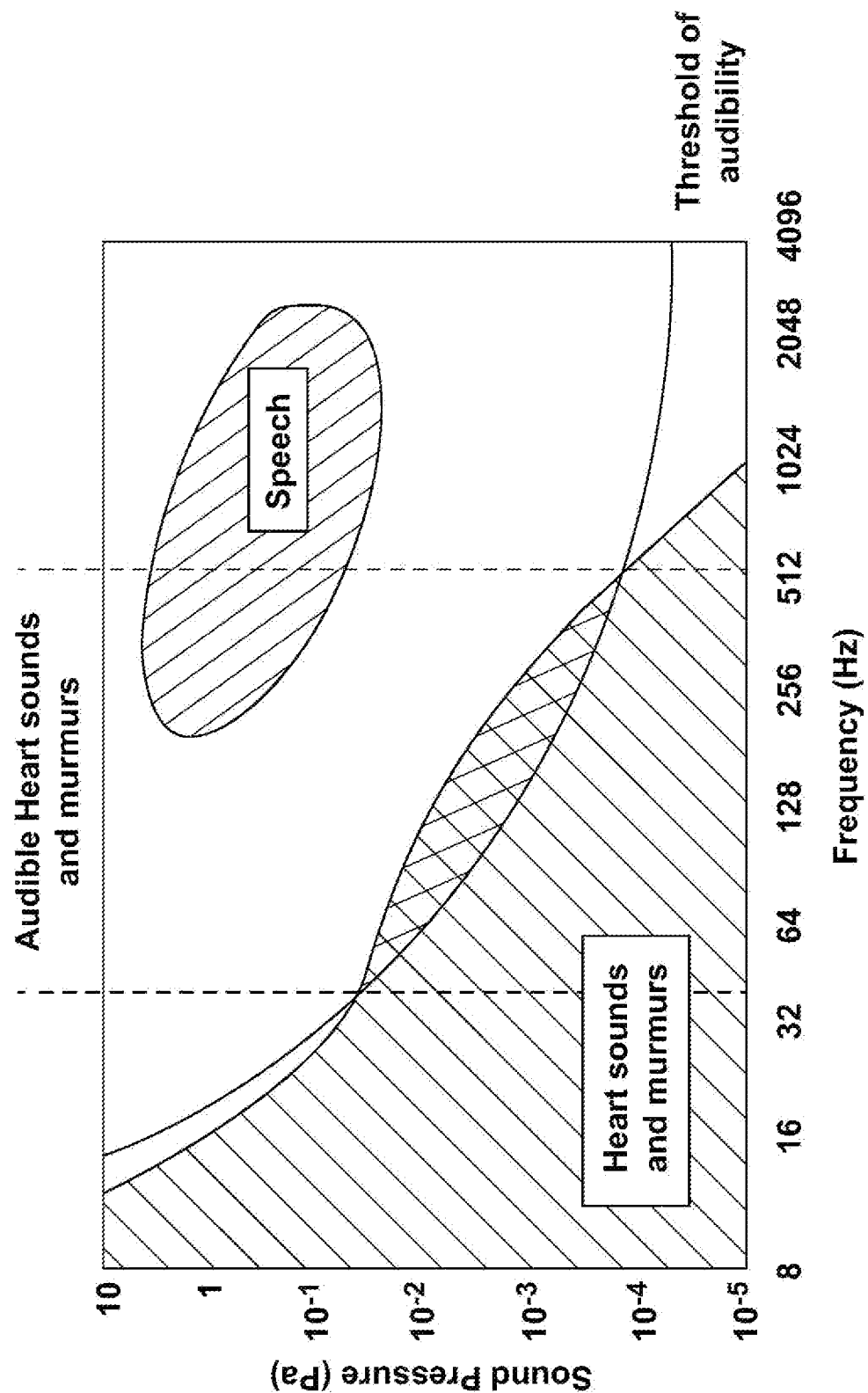
FIG. 4 depicts a representation of regions of Pressure-Frequency domain where heart sounds, murmurs and speech are typically located.

To better illustrate this, reference will now be made to FIG. 4 depicting a graphical representation 400. The graphical representation 400 illustrates regions of Pressure-Frequency domain where heart sounds, murmurs and human speech are typically located. In addition, the graphical representation 400 depicts a human audibility threshold. Developers of the present technology have realized that, a portion of the frequency spectrum that carries information of interest about the heart is below the range of human hearing. As a result, the medical practitioner 220 may be unable to appreciate at least some information of interest about the heart since her/his auditory capabilities are limited to the human auditory frequency spectrum.

For that purpose, developers of the present technology have devised methods and devices for processing a waveform signal associated with the patient 210 such that a portion of the waveform signal is, in a sense, "shifted" to a human-audible frequency range. It should be noted that the human-audible frequency range is between 20 Hz and 20 000 Hz.

For example, methods and systems disclosed herein may allow (i) identifying a portion of the waveform signal 310 that carries information of interest, and (ii) generating a corresponding enhanced portion in a comparatively higher frequency range (which is in the human-audible frequency range) and which is used instead of the original portion in the modified waveform signal 320. As a person skilled having appreciated the present disclosure will understand that such processing by the processor 110 of the electronic device 250 may significantly improve sound perception of the phonocardiogram signal by the medical practitioner 220 (e.g., the human operator).

How the processor 110 of the electronic device 250 is configured to implement the sound processing computer-implemented procedure 350 will now be described in greater detail with reference to FIG. 5. As seen, there is depicted a representation 500 of sound data processing performed by the plurality of sound processing computer-implemented procedures 350 on the waveform signal 310.

Figure 6:
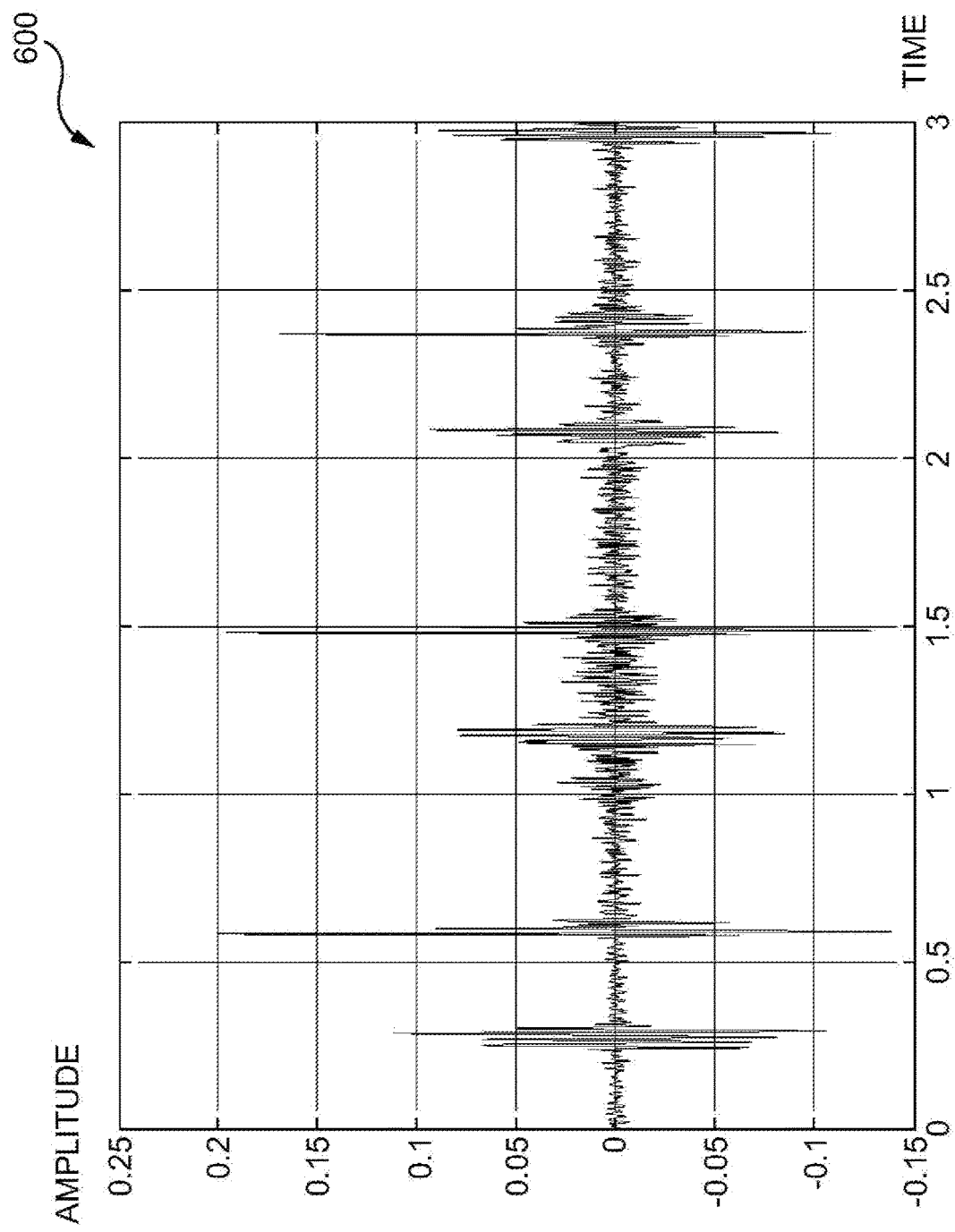
FIG. 6 depicts a time-domain representation of the waveform signal of FIG. 3, in accordance with one non-limiting implementation of the present technology.
Figure 7:
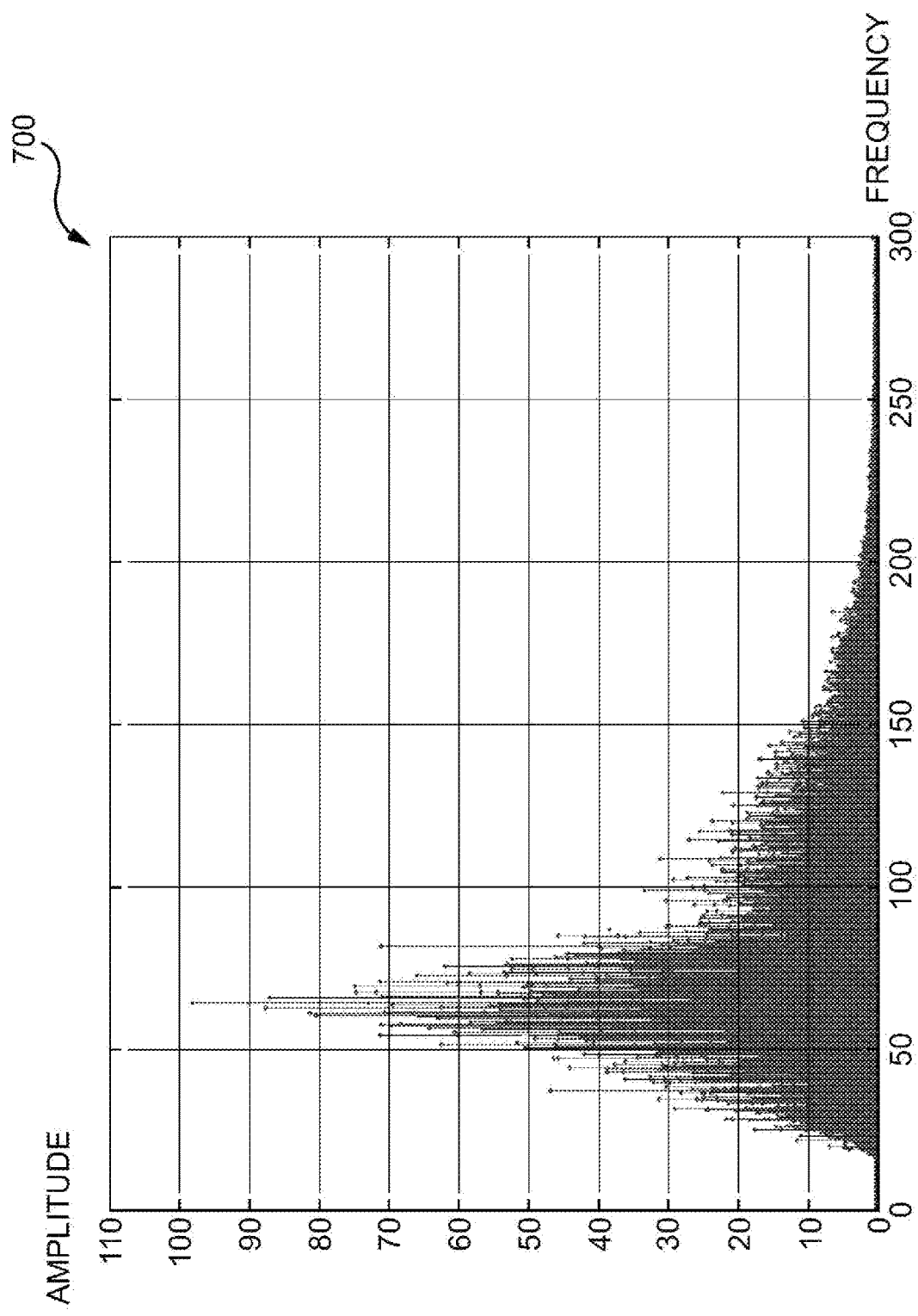
FIG. 7 depicts a frequency-domain representation of the waveform signal of FIG. 3, in accordance with one non-limiting implementation of the present technology.

The waveform signal 310 is depicted on FIG. 6 in a time-domain representation 600 thereof, in accordance with one non-limiting implementation of the present technology. The waveform signal 310 is depicted on FIG. 7 in a frequency-domain representation 700 thereof, in accordance with one non-limiting implementation of the present technology. It should be noted that although the frequency-domain representation 700 is depicted for illustrating some functionalities of the plurality of sound processing computer-implemented procedures 350, it should be noted that sound data processing performed in the context of the present technology occurs in the time-domain, as opposed to performing frequency-domain processing of the waveform signal 310.

Figure 5:
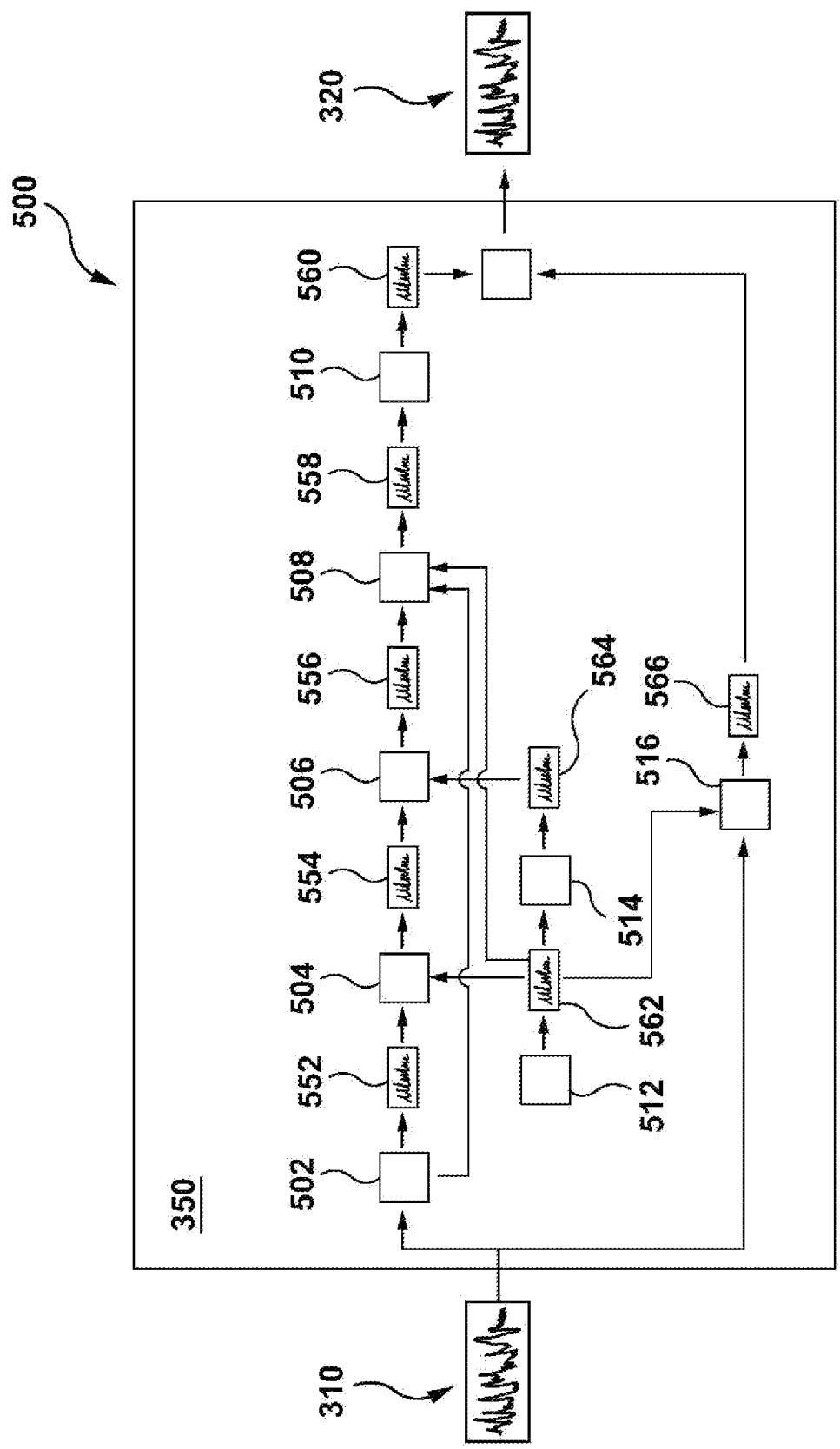
FIG. 5 depicts a representation of how a plurality of sound processing computer-implemented procedures are used to generate the modified waveform signal of FIG. 3, in accordance with at least some non-limiting embodiments of the present technology.

Returning to the description of FIG. 5, the processor 110 may use the waveform signal 310 as input for a first filtering operation 502. Broadly speaking, the processor 110 may be configured to perform the first filtering operation 502 by applying a computer-implemented frequency filter having a respective cut-off frequency value. The purpose of the first filtering operation 502 is to cut-off low frequencies from the waveform signal 310. The low frequencies may carry less or no information of interest. In one non-limiting implementation of the present technology, the cut-off frequency value associated with the first filtering operation 502 may be 5 Hz. In other words, the processor 110 may be configured to use the first filtering operation 502 for removing from the waveform signal 310 a portion having frequencies below the respective cut-off frequency value of 5 Hz.

However, this might not be the case in each and every implementation of the present technology. In other examples, the first cut-off frequency value employed during the first filtering operation 502 may be between 5-20 Hz and up to 100 Hz in further examples.

It can be said that at least some embodiments of signal processing disclosed herein may allow operation of the electronic device in both a bell mode and in a diaphragm mode simultaneously. In other words, at least some signal processing techniques disclosed herein may allow transforming a waveform such that the modified version thereof carries information that is detectable (i) in a bell mode of operation and also (ii) in a diaphragm mode of operation.

Figure 8:
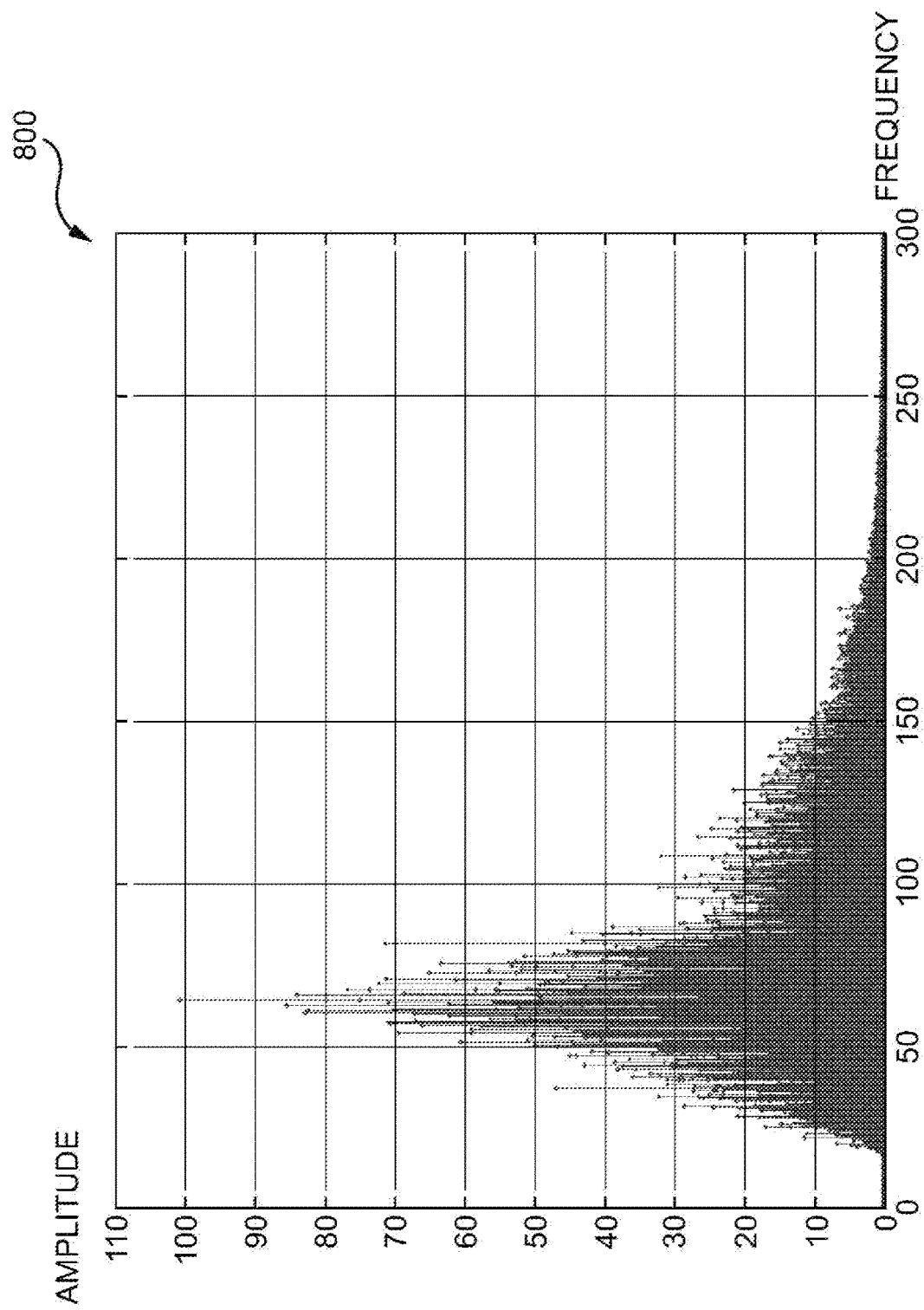
FIG. 8 depicts a frequency-domain representation of a first intermediate signal, in accordance with one non-limiting implementation of the present technology.

In response to applying the first filtering operation 502, the processor 110 is configured to generate a first intermediate signal 552. For example, the first intermediate signal 552 is depicted on FIG. 8 in a frequency-domain representation 800 thereof, in accordance with one non-limiting implementation of the present technology.

The processor 110 is also configured to execute a frequency-shift determination procedure 512. Broadly speaking, the frequency-shift determination procedure 512 is used for determining a "frequency-shift" (FS) value 562. The purpose of the frequency-shift determination procedure 512 is to determine the amount of "frequency shift" towards higher frequencies that a particular portion of the waveform signal 310 is to undergo. In one example, after undergoing the frequency shift towards the higher frequencies, the particular portion of the waveform signal 310 may become audible to a human.

In some embodiments of the present technology, it is contemplated that the FS value 562 may range from 10 Hz to 100 Hz. For example, the FS value 562 may be 45 Hz in one implementation of the present technology. In further embodiments of the present technology, the medical practitioner 220 may provide an input to the processor 110 that is configured to use the input as an input into the frequency-shift determination procedure 512. This means that the medical practitioner 220 may provide an indication of the FS value 562 to the processor 110. For example, the medical practitioner 220 may select a given FS value depending on a type of bodily sounds (s)he is trying to observe. In other embodiments, the FS value 562 may be a pre-determined value stored in the memory 130 for future use thereof by the processor 110. It is contemplated that the FS value 562 may be pre-determined based on how audible the effect of frequency shift will be for the medical practitioner. For example, the smaller the FS value is, the less audible the effect of the frequency shift will be to the medical practitioner. In the same example, the larger the FS value is, the more unusual the modified signal will be.

In some embodiments of the present technology, additional sound processing procedures may be performed by the processor 110 in order to increase the gain of the modified signal. For example, the processor 110 may increase the power and/or amplitude of the modified signal without departing from the scope of the present technology.

The processor 110 is also configured to execute a second filtering operation 504. As illustrated, the processor 110 is configured to use the first intermediate signal 552 and the FS value 562 as inputs for the second filtering operation 504. Broadly speaking, the processor 110 may be configured to execute the second filtering operation 504 by applying a computer-implemented frequency filter having a frequency-shift-dependent-cut-off frequency value—that is, the cut-off frequency value of the second filtering operation 504 can be a value that depends on the FS value 562.

In some embodiments, the processor 110 may determine the frequency-shift-dependent-cut-off frequency value for the second filtering operation 504 as being two times larger than the FS value 562. For example, if the FS value 562 is 45 Hz, the processor 110 may determine the frequency-shift-dependent-cut-off frequency value for the second filtering operation 504 to be 90 Hz, in one non-limiting implementation of the present technology. In other examples, the second cut-off frequency value employed by the processor 110 for performing the second filtering operation 504 may range between 40 Hz and 200 Hz, or in further examples, between 70 Hz and 130 Hz.

The purpose of the second filtering operation 504 is to cut off frequencies of the first intermediate signal 552 that are above the frequency-shift-dependent-cut-off frequency value. As a result, the processor 110 may be configured to generate a second intermediate signal 554. In at least some embodiments of the present technology, it can be said that the second intermediate signal 554 is the waveform signal 310 without frequencies below the cut-off frequency value of the first filtering operation 502 and without frequencies above the frequency-shift-dependent-cut-off frequency value. It can also be said that the second intermediate signal 554 represents the portion of the waveform signal 310 that is to be shifted to higher frequencies so as to become audible in the modified waveform signal 320.

Figure 9:
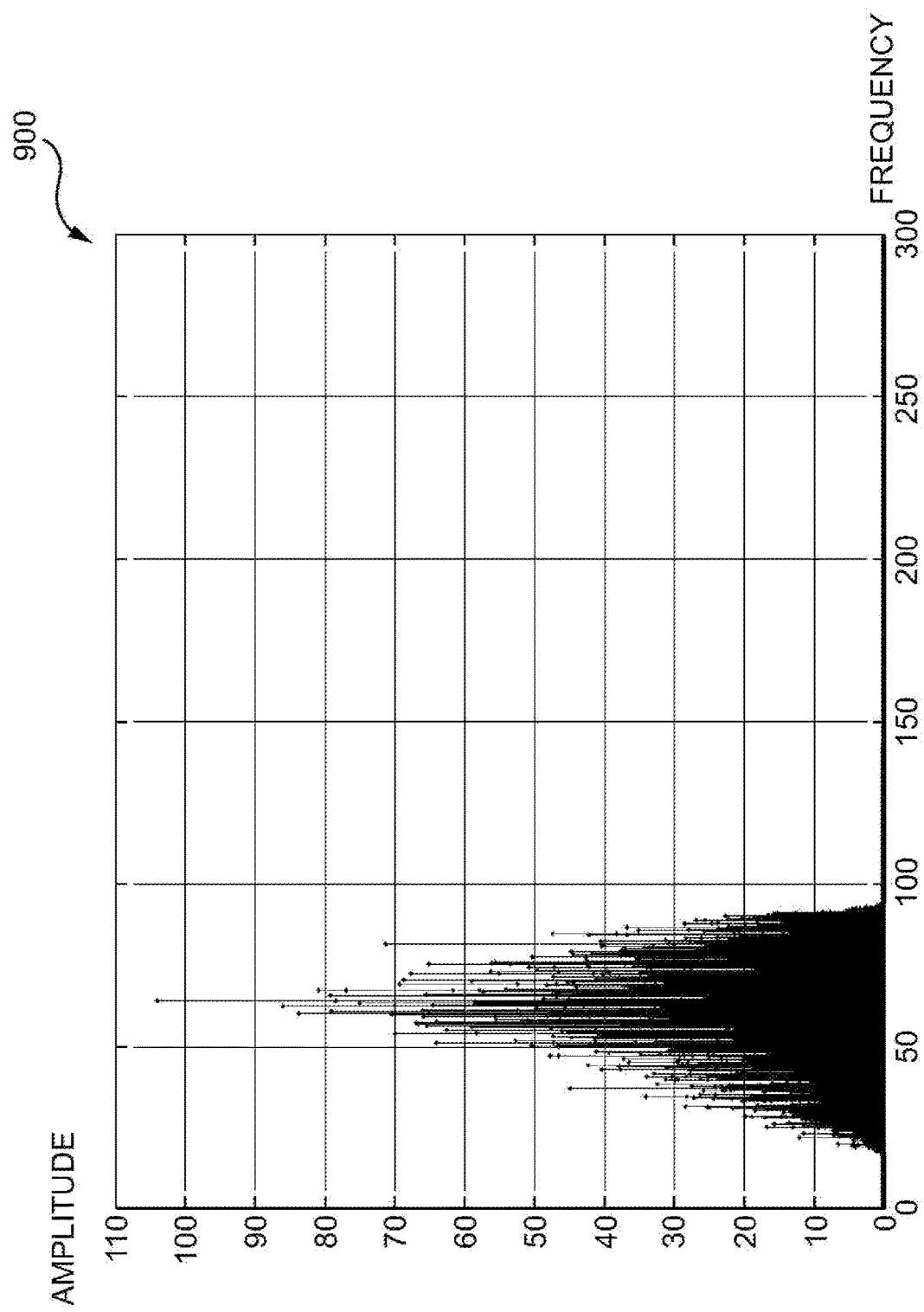
FIG. 9 depicts a frequency-domain representation of a second intermediate signal, in accordance with one non-limiting implementation of the present technology.

For example, the second intermediate signal 554 is depicted on FIG. 9 in a frequency-domain representation 900 thereof, in accordance with one non-limiting implementation of the present technology. As seen, the second intermediate signal 554 does not include frequencies above 90 Hz.

Figure 10:
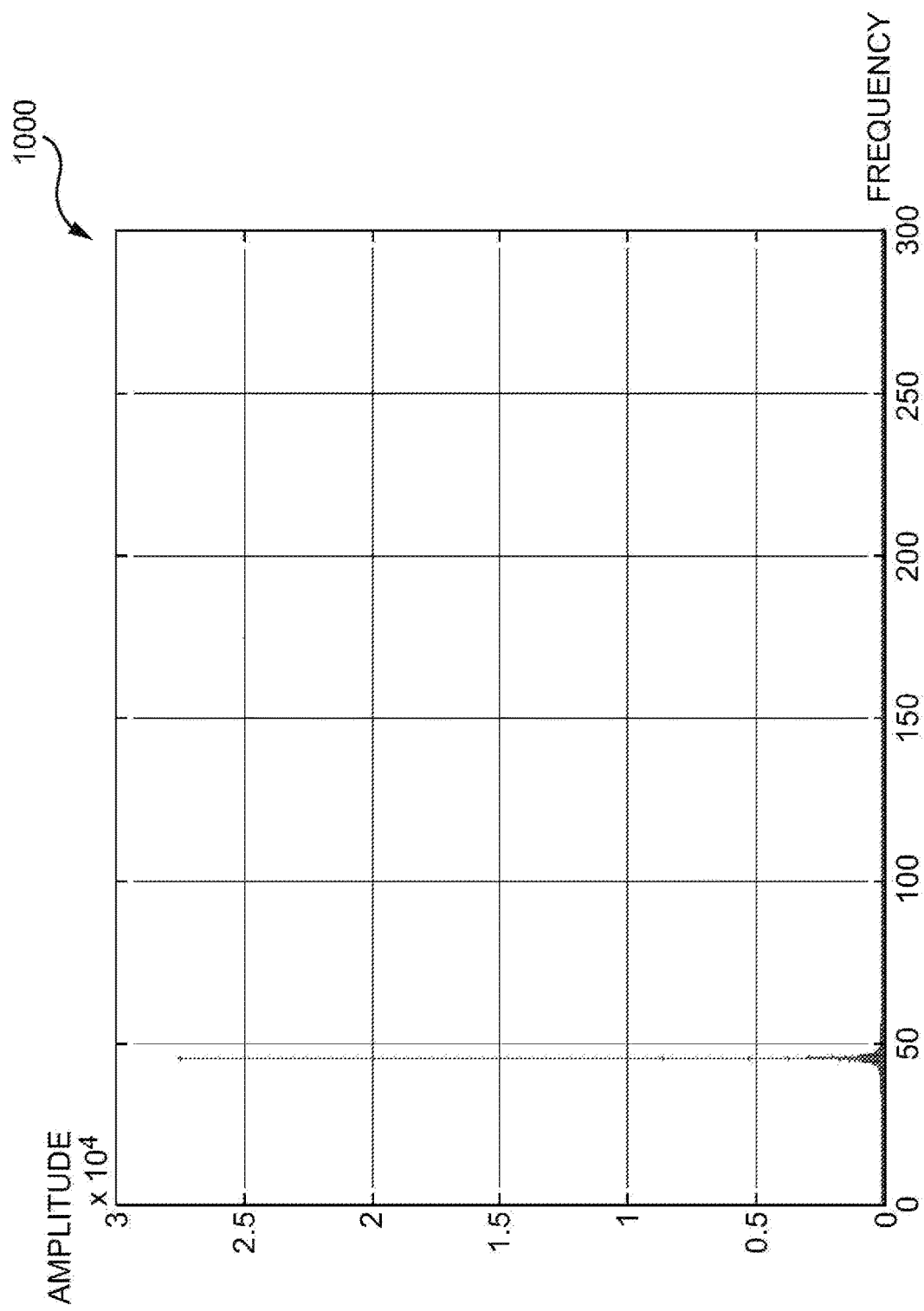
FIG. 10 depicts a frequency-domain representation of a modulation signal, in accordance with one non-limiting implementation of the present technology.

The processor 110 is also configured to execute a modulation signal generation procedure 514. Broadly speaking, the modulation signal generation procedure 514 generates a given modulation signal to be used for modulating the second intermediate signal 554. The processor 110 is configured to use the FS value 562 as input for the modulation signal generation procedure 514, and which outputs a modulation signal 564. It should be noted that the processor 110 can generate the modulation (carrier) signal 564 in a form of a sinusoidal wave having a frequency equal to the FS value 562. For example, the modulation signal 564 may be a sinusoidal wave having a frequency of 45 Hz, as seen on FIG. 10 depicting a frequency-domain representation 1000 thereof. The time length of the modulation signal 564 is equal to the time length of the waveform signal 310.

Figure 11:
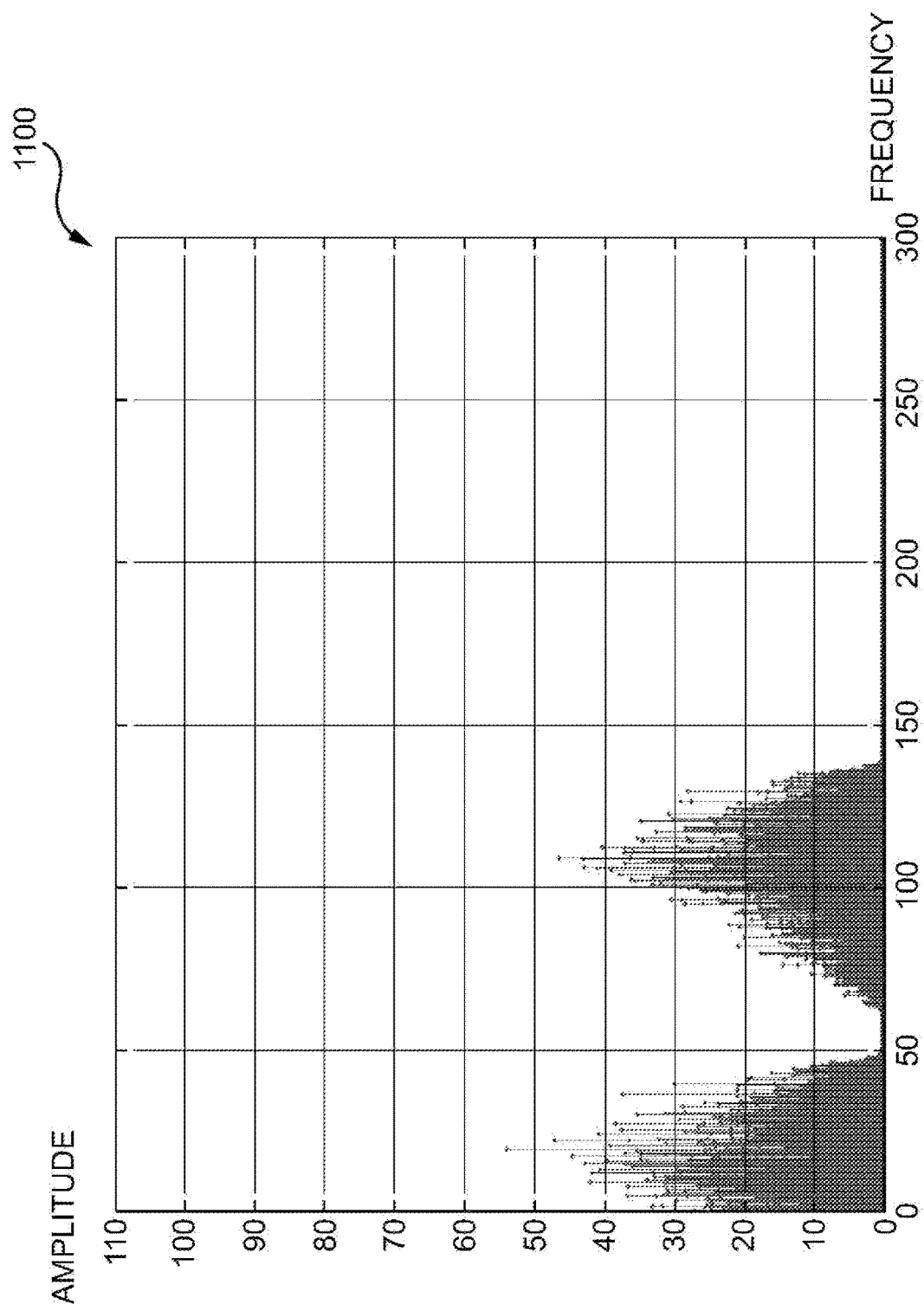
FIG. 11 depicts a frequency-domain representation of a first modulated intermediate signal, in accordance with one non-limiting implementation of the present technology.

The processor 110 is configured to perform a modulation procedure 506. The processor 110 is configured to use the second intermediate signal 554 and the modulation signal 564 as input for the modulation procedure 506. Broadly speaking, the purpose of the modulation procedure 506 is to modulate the second intermediate signal 554 using the modulation signal 564 as a carrier signal. As a result, the processor 110 is configured to generate a first modulated intermediate signal 556. For example, the first modulated intermediate signal 556 is depicted on FIG. 11 in a frequency-domain representation 1100 thereof.

The first modulated intermediate signal 556 includes (i) a first frequency portion 1110, and (ii) a second frequency portion 1120. These two portions, also referred to as negative and positive frequency portions of a modulated signal in certain embodiments, occur due to the modulation operation procedure 506. It should be noted that a first frequency portion 1110, and (ii) a second frequency portion 1120 are on respective sides of the frequency value of the modulation signal 564. In other words, since in this example the modulation signal 564 has a frequency of 45 Hz, the first frequency portion 1110 is located on the one side of the frequency value of 45 Hz (e.g. below 45 Hz), while the second frequency portion 1120 is located on the other (opposite) side of the frequency value of 45 Hz (e.g. above 45 Hz).

It is important to note that due to how the first filtering operation 502 and the second filtering operation 504 can be applied such that when the second intermediate signal 554 is modulated via the modulation signal 564, the first frequency portion 1110 and the second frequency portion 1120 of the first modulated intermediate signal 556 do not overlap each other.

It should be noted that, unlike the signal shift techniques used in some radio communication technologies, the problem of overlapping positive and negative frequency portions after modulation seems not to occur, in certain embodiments, since the amount of frequency shift in those situations is larger than the frequency range (frequency range of the second intermediate signal 554) being shifted. It should also be noted that frequency shifts in radio communication technologies are by an order of magnitude larger than 45 Hz. For at least that reason, modulation performed in radio communication systems may not require the first filtering operation 502 and the second filtering operation 504, as described above.

Developers of the present technology have realized that without isolation of the second intermediate signal 554 via execution of the first and the second filtering operations 502 and 504, the first frequency portion 1110 and the second frequency portion 1120 could overlap with each other. Such an overlap of the first frequency portion 1110 (to be further used for generating the modified waveform signal 320) by the second frequency portion 1120 would introduce additional noise into the modified waveform signal 320 and which is undesirable for augmenting auditory capabilities of the medical practitioner 220. As such, in at least some embodiments of the present technology, developers of the present technology have devised methods and systems that can in a sense, "prepare" the second intermediate signal 554 in a way that ensures that the first frequency portion 1110 and the second frequency portion 1120 are found exclusively on respective sides of the carrier signal frequency, and hence, do not overlap.

Returning to the description of FIG. 5, the processor 110 may also be configured to apply a third filtering operation 508 onto the first modulated intermediate signal 556. Broadly speaking, the purpose of the third filtering operation 508 is to use a third cut-off frequency value to cut off the second frequency portion 1120 (and potentially a frequency peak corresponding to the carrier signal) from the first modulated intermediate signal 556.

Figure 12:
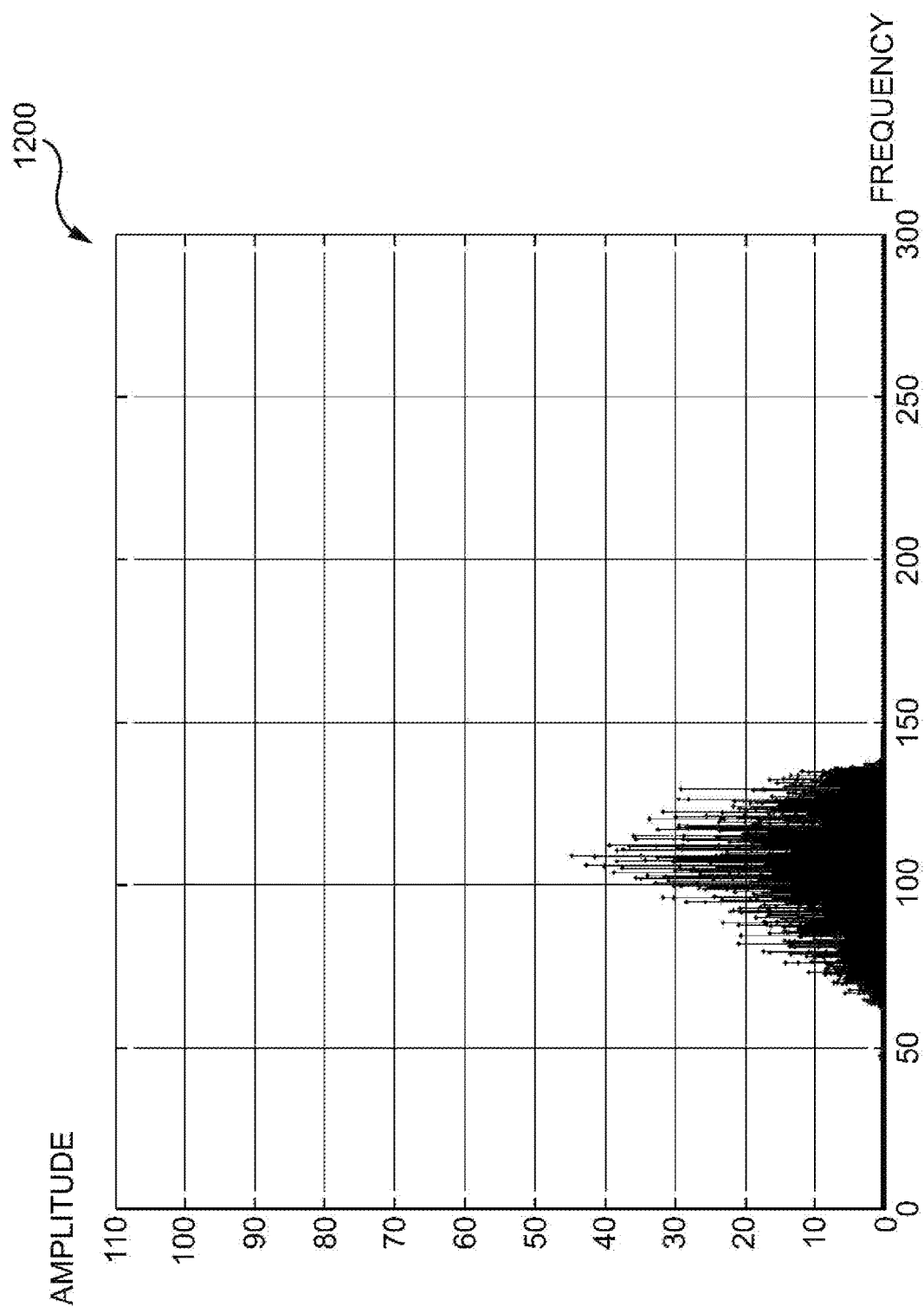
FIG. 12 depicts a frequency-domain representation of a second modulated intermediate signal, in accordance with one non-limiting implementation of the present technology.

It should be noted that the processor 110 may use the first cut-off frequency value from the first filtering operation 502 and the FS value 562 as inputs for the third filtering procedure 508. The processor 110 may determine the third cut-off frequency value as a combination (e.g., a sum) of the first cut-off frequency value and the FS value 562. For example, the processor 110 may determine the third cut-off frequency value to be 50 Hz, in one non-limiting implementation of the present technology. As a result of the third filtering operation 508, the processor 110 may be configured to generate a second modulated intermediate signal 558. For example, the second modulated intermediate signal 558 is depicted on FIG. 12 in a frequency-domain representation 1200 thereof.

The processor 110 may be configured to execute a normalization procedure 510 on the second modulated intermediate signal 558. In some cases, the processor 110 may be configured to execute the normalization procedure 510 on the second modulated intermediate signal 558 in order to remedy the signal energy loss resulting from the filtering of the second portion 1120 (e.g., negative frequency spectrum) from the first modulated intermediate signal 556 via the third filtering operation 508. For example, the processor 110 executing the normalization procedure 510 may be configured to increase two-fold the amplitude of the second modulated intermediate signal 558. The processor 110 executing the normalization procedure 510 may be configured to generate a normalized signal 560.

The processor 110 is also configured to execute a fourth filtering operation 516 onto the waveform signal 310. Broadly speaking, the purpose of the fourth filtering operation 516 is to apply a fourth cut-off frequency value onto the waveform signal 310 in order to generate a high-frequency signal 566. It should be noted that executing the fourth filtering operation 516, the processor 110 may isolate a portion of the waveform signal 310 that is above the fourth cut-off frequency value.

Figure 13:
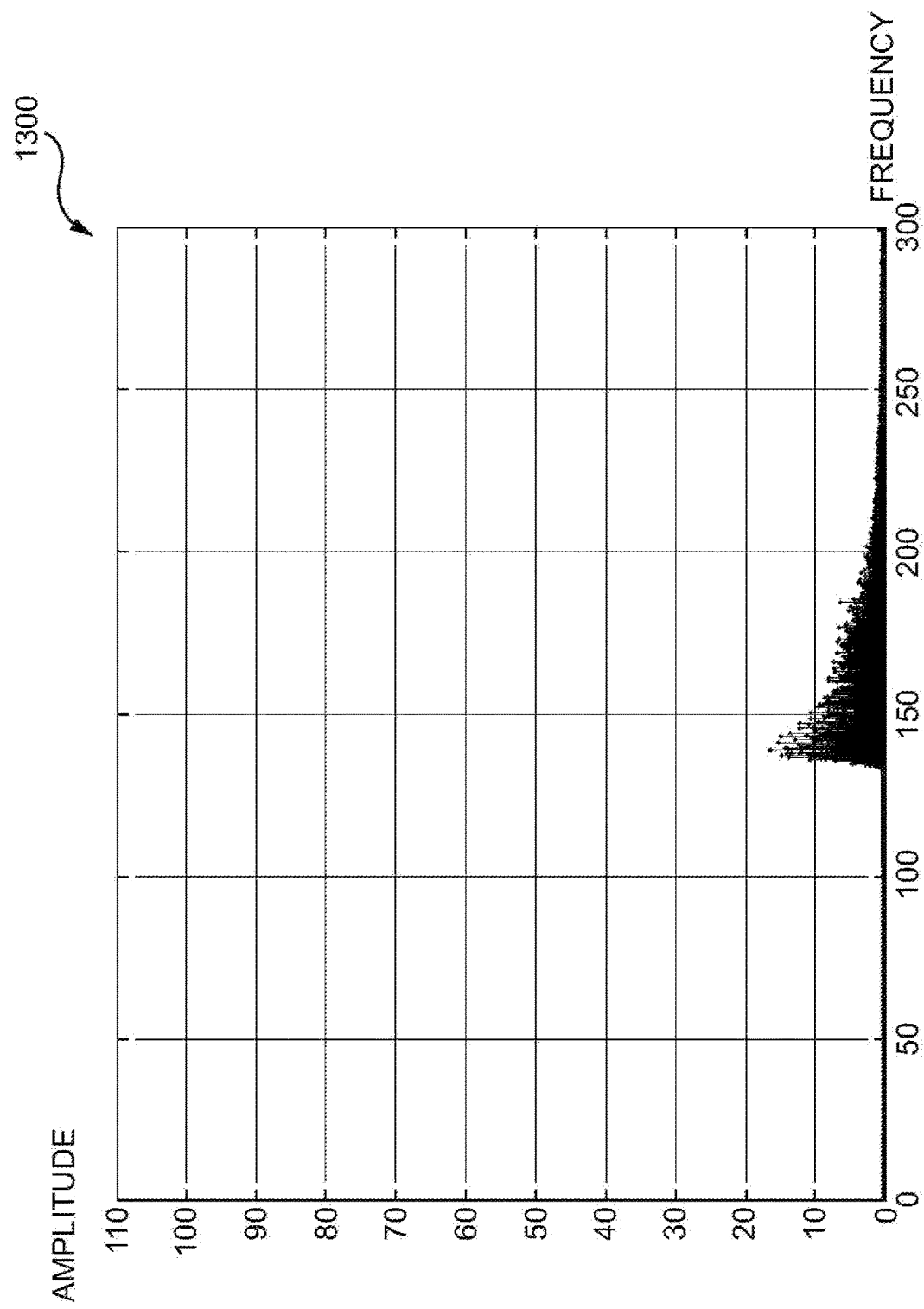
FIG. 13 depicts a frequency-domain representation of a high-frequency signal, in accordance with one non-limiting implementation of the present technology.

In some embodiments, the fourth cut-off frequency value may be dependent on the FS value 562. For example, the fourth cut-off frequency value may be equal to three times the FS value 562, in one non-limiting implementation of the present technology. The high-frequency signal 566 is depicted on FIG. 13 in a frequency-domain representation 1300 thereof.

Figure 14:
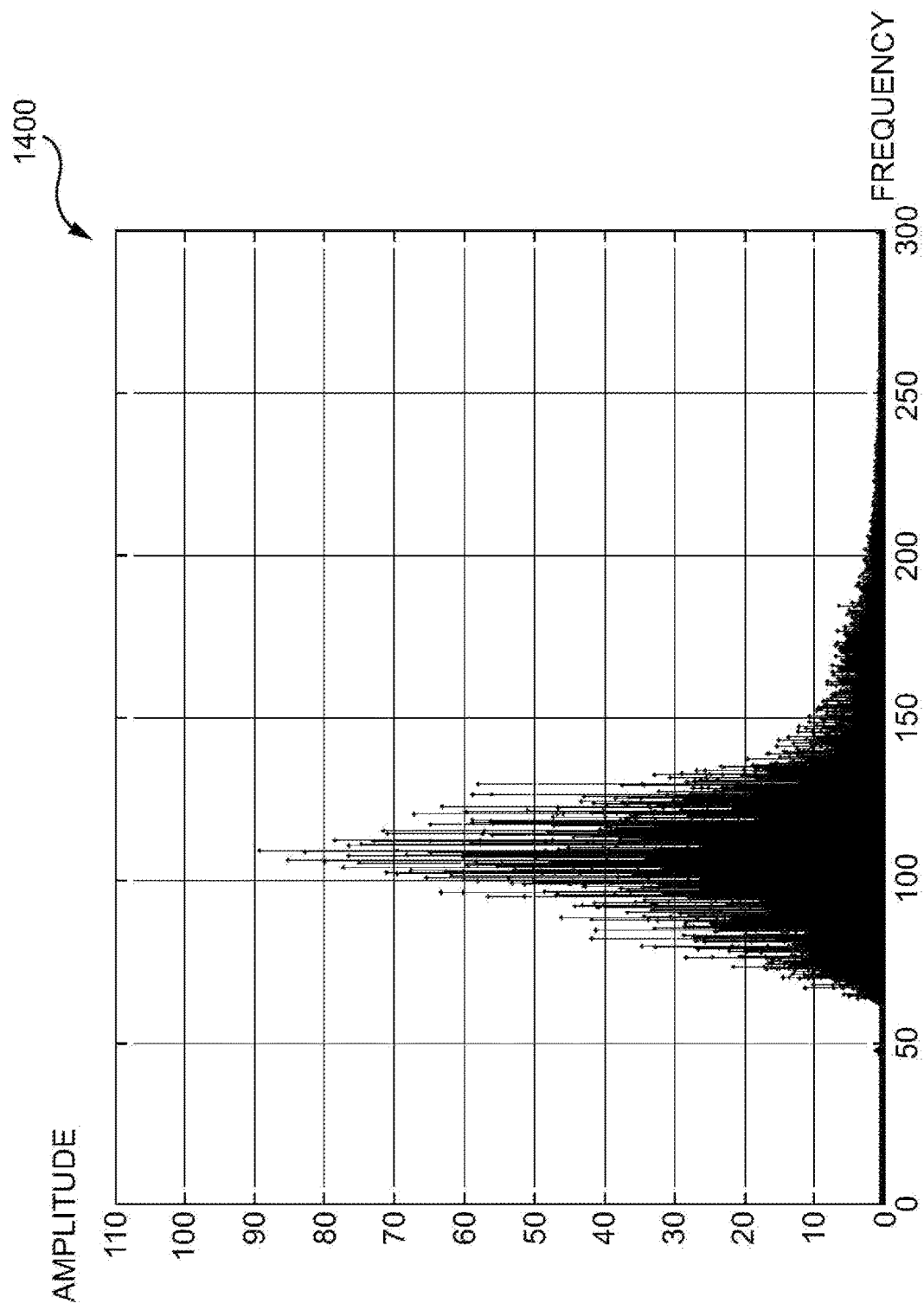
FIG. 14 depicts a frequency-domain representation of the modified waveform signal of FIG. 3, in accordance with one non-limiting implementation of the present technology.
Figure 15:
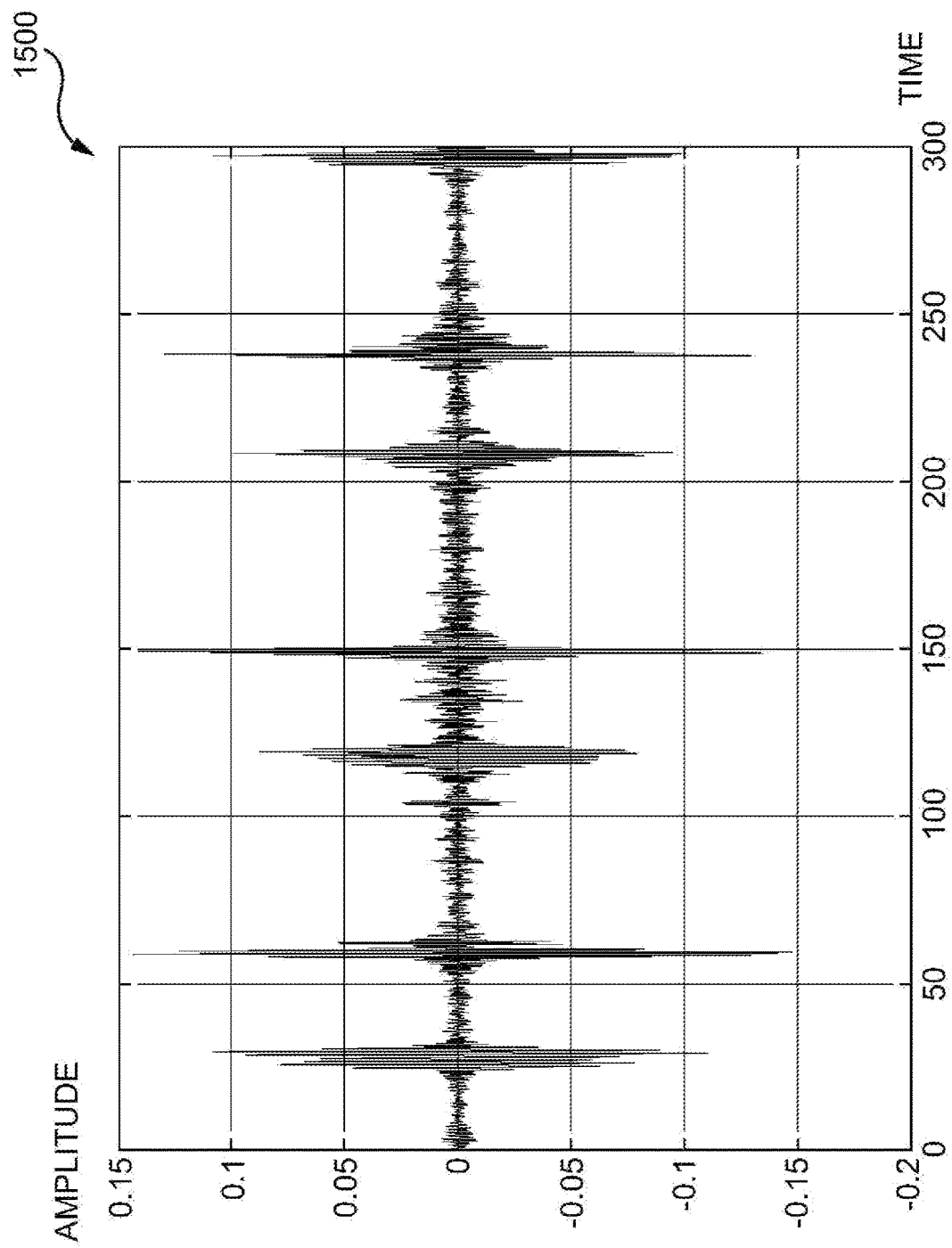
FIG. 15 depicts a time-domain representation of the modified waveform signal of FIG. 3, in accordance with one non-limiting implementation of the present technology.

The processor 110 may then be configured to execute a combination procedure 518 during which the normalized signal 560 is combined with the high-frequency signal 566. Broadly speaking, the processor 110 is configured to combine a portion of the waveform signal 310 that is audible (e.g., the high-frequency signal 566) with a processed portion of the waveform signal 310 which is now in the human-audible range (the normalized signal 560). As a result, the processor 110 may be configured to generate the modified waveform signal 320. For example, the modified waveform signal 320 is depicted on FIG. 14 in a frequency-domain representation 1400 thereof and on FIG. 15 in a time-domain representation 1500 thereof.

In at least some embodiments of the present technology, the processor 110 may be configured to perform time domain filtering of digital audio signals via one or more filtering operations disclosed herein. It is also contemplated that other processing operations, in addition to filtering operations, may be implemented in the time domain, rather than using time-to-frequency conversions for performing filtering and/or processing in the frequency domain and re-converting back into the time domain.

Figure 16:
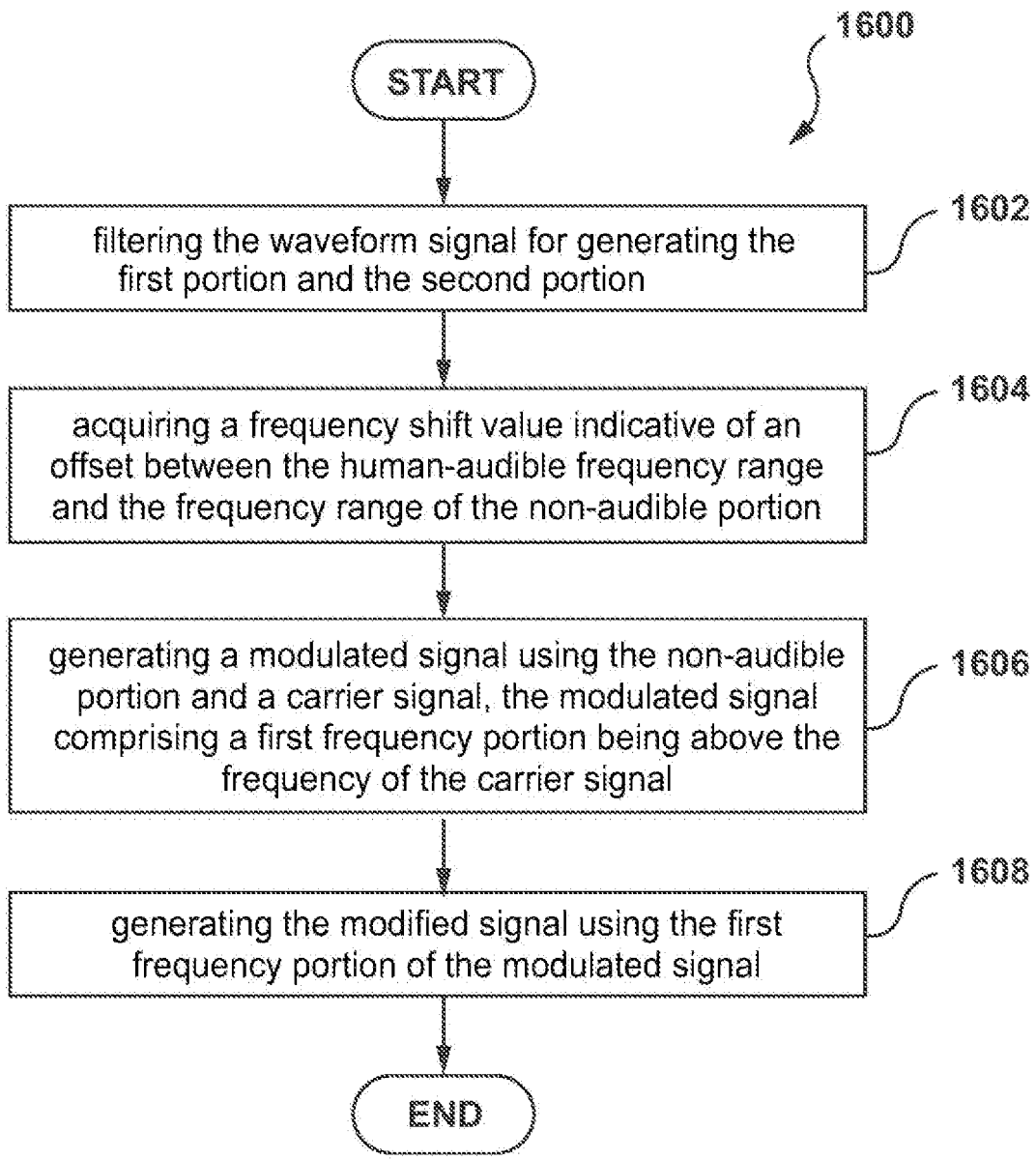
FIG. 16 is a scheme-block representation of a method executable by a processor of FIG. 1, in accordance with at least some non-limiting embodiments of the present technology.

In some embodiments of the present technology, the processor 110 of FIG. 1 may be configured to execute a method 1600 depicted on FIG. 16. Various steps of the method 1600 will now be described in turn.

Step 1602: Filtering the Waveform Signal for Generating the First Portion and the Second Portion The method 1600 begins at step 1602 with the processor 110 of the electronic device 250 configured to determine/acquire one or more cut-off frequency values for filtering the waveform signal 310. As a result, the processor 110 is configured to generate a second portion of the waveform signal 310, such as the high-frequency signal 566 and a first portion of the waveform signal 310, such as the second intermediate signal 554. It is contemplated that the processor 110 may acquire the FS value 562 prior to and/or during the step 1602.

As previously alluded to, the first portion of the waveform signal 310 may be a non-audible portion of the waveform signal 310 and the second portion of the waveform signal 310 may be an audible portion of the waveform signal 310.

In some embodiments, the processor 110 may be configured to determine the one or more cut-off frequency values based on an input from a human operator (e.g., the medical practitioner 220). For example, the human operator may be configured to input one or more frequency values to be used by the first filtering operation 502, the second filtering operation 504, and the fourth filtering operation 516. Alternatively the frequency values may be predetermined and otherwise obtained by the processor.

In other embodiments, the processor 110 is configured to filter the waveform signal 310 by employing the first cut-off frequency value and the second cut-off frequency value for isolating (generating) the first portion of the waveform signal 310 (e.g., the second intermediate signal 554). For example, the processor 110 may determine the first cut-off frequency value to be 5 Hz and the second pre-determined cut-off frequency value to be 90 Hz. It is contemplated that in at least some embodiments, the processor 110 may be configured to determine the second cut-off frequency value based on the FS value 562.

In further embodiments, the processor 110 configured to filter the waveform signal 310 by employing the fourth cut-off frequency value for isolating (generating) the second portion of the waveform signal 310 (e.g., the high-frequency signal 566). For example, the processor 110 may determine the fourth cut-off frequency value to be 135 Hz. It is contemplated that in at least some embodiments, the processor 110 may be configured to determine the fourth cut-off frequency value based on the FS value 562.

Step 1604: Acquiring a Frequency Shift Value Indicative of a Frequency Range by which the First Portion is to be Shifted to Frequencies Above the First Frequency Range The method 1600 continues to step 1604 with the processor 110 configured to acquire the FS value 562. It should be noted that the FS value 562 is value indicative of a frequency range by which the first portion is to be shifted to frequencies above the first frequency range.

It can be said that the FS value 564 may be indicative of how much the frequencies of the first frequency range are to be moved towards higher frequencies. In some cases, this may be performed in order to shift the first portion from its current frequency range into the human-audible frequency range.

In some embodiments, the FS value 562 may be acquired from a memory associated with the electronic device 250. For example, the FS value 562 may have been determined and previously stored in the memory for future use thereof. In other embodiments, the FS value 562 may acquired as an input of the human operator. For example, the FS value 562 may be 45 Hz. In another example, the FS value 562 may be a frequency value between 10 Hz and 100 Hz.

It should be noted that the human-audible frequency range is between 20 Hz and 20,000 Hz. However, it should be noted that a portion of the waveform signal 310 to be shifted to higher frequencies may be at least partially in the human-audible frequency range. In these cases, the FS value 562 may be selected for shifting this portion of the waveform signal 310 to higher frequencies such that the frequency range of the resulting modified portion in the modified waveform signal 320 is completely inside the human-audible frequency range.

Step 1606: Generating a Modulated Signal Using the First Portion and a Carrier Signal, the Modulated Signal Comprising a First Frequency Portion being Above the Frequency of the Carrier Signal The method 1600 continues to step 1606 with the processor 110 configured to generate a modulated signal (e.g., the first modulated intermediate signal 556) using the first portion and the modulation signal 564. The modulation signal 564 has a frequency equal to the FS value 562 and a time-length equal to a time-length of the waveform signal 310.

It should be noted that the first modulated intermediate signal 556 comprises the first frequency portion 1110 (see FIG. 11) being in a frequency range that is above the FS value 562 and a second frequency portion 1120 being in a frequency range that is below the FS value 562.

It should also be noted that the one or more cut-off frequency values (the first and the second cut-off frequency values of the first and the second filtering operation 502 and 504, respectively) have been determined for ensuring that the first frequency portion 1110 (e.g., positive frequency spectrum after modulation) and the second frequency portion 1120 (e.g., negative frequency spectrum after modulation) are in non-overlapping frequency ranges of the modulated signal (e.g., the first modulated intermediate signal 556).

In at least some embodiments of the present technology, it is contemplated that the one or more cut-off frequency values (the first and the second cut-off frequency values of the first and the second filtering operation 502 and 504, respectively) have been determined so that the first frequency portion 1110 (e.g., positive frequency spectrum after modulation) and the second frequency portion 1120 (e.g., negative frequency spectrum after modulation) are in substantially non-overlapping frequency ranges of the modulated signal (e.g., the first modulated intermediate signal 556). This means that in some implementations of the present technology, a minimum overlap between a first frequency portion and a second frequency portion may be acceptable during signal processing. For example, an overlap of 0.5% may be acceptable during signal processing. However, it should be noted that the larger the overlap, the more noise may be inadvertently introduced during the signal processing techniques disclosed herein.

In some embodiments, the processor 110 may be configured to filter, by employing the third cut-off frequency value (of the third filtering operation 508) the first modulated intermediate signal 556 for isolating (generating) the first frequency portion 1110 (e.g., the second modulated intermediate signal 558). The third cut-off frequency value may depend on the first cut-off frequency value and the FS value 562 (e.g., a sum thereof). In one example, the third cut-off frequency value may be 50 Hz.

It should be noted that the first frequency portion 1110 (e.g., the second modulated intermediate signal 558) is a modified representation of the first portion from the waveform signal 310, and the frequency range of the first frequency portion 1110 (e.g., the second modulated intermediate signal 558) is inside the human-audible frequency range.

Step 1608: Generating the Modified Signal Using the First Frequency Portion of the Modulated Signal The method 1600 continues to step 1608 with the processor 110 configured to generate the modified waveform signal 320 using the first frequency portion 1110. In some embodiments, the processor 110 may be configured to generate the modified waveform 320 as a combination of the second portion (e.g., the high-frequency signal 566) and the first frequency portion 1110 (e.g., the second modulated intermediate signal 558). In other words, the processor 110 may trigger the electronic device to reproduce at least one of the first frequency portion 1110 to a human operator and a combination of the first frequency portion 1110 and the second portion (e.g., the high-frequency signal 566). In some embodiments, the processor 110 configured to generate the modified waveform signal 320 as a combination of the high-frequency signal 566 and the normalized signal 560 (being determined based on the second modulated intermediate signal 558 as explained above).

In some embodiments, the processor 110 may be configured to (as part of the step 1608) generate the normalized signal 560 based on the first frequency portion 1110 (e.g., the second modulated intermediate signal 558), and generate the modified waveform signal 320 as a combination of the normalized signal 560 and the second portion (e.g., the second modulated intermediate signal 558).

In some embodiments, the processor 110 may be configured to store the modified waveform signal 320 in the memory 130 of the electronic device 250 and/or a remote memory. In other embodiments, the processor 110 may be configured to trigger generation of sound representative of the modified waveform signal 320 for the human operator. For example, the processor 110 may trigger one or more speakers of the electronic device 250 to reproduce sound representative of the modified waveform signal 320 for the medical practitioner 220. In some embodiments, the electronic device 250 having the processor 110 may be an electronic stethoscope.

In at least some embodiments of the present technology, it is contemplated that a plurality of first portions from the waveform signal 310 may be generated, similarly to the first portion (e.g., the second intermediate signal 554), and may be shifted to higher frequencies, similarly to how the first portion of the waveform signal 310 is shifted to higher frequencies.

In at least some embodiments, the processor 110 may be configured to filter, similarly to what has been described above, the waveform signal 310 to remove the second portion (e.g., the high-frequency signal 566) and low frequencies (below 5 Hz, for example). Also, as described above, the processor 110 may acquire a given FS value. In some cases, the given FS vale may be between 10 and 100 Hz.

In those embodiments where the processor is configured to shift the plurality of first portions from the waveform signal 310, the processor 110 may also determine an inter-portion value, herein sometimes referred to as "Fad", which is a value representative of a frequency range between the respective first portions to be selected. For example, the inter-portion value may be between 1 and 20 Hz. In another example, the inter-portion value is 2 Hz. In this example, this means that the first portions from the plurality of portions are associated with respective frequency ranges in the waveform signal 310 that are spaced apart by 2 Hz. It should be noted that in some cases, smaller inter-portion values may result in less information loss during processing of the waveform signal 310.

The processor 110 may also be configured to select a number "N" of first portions in the plurality of portions to be shifted. For example, the number N of first portions may be determined based on a frequency band of the waveform signal 310 (Fsignal) and the FS value 524. In one implementation, the number N of first portions may be determined as N=Fsignal/(2*Fs) value, and which can be rounded to a larger integer.

In some embodiments, the processor 110 may be configured to acquire a pre-determined number "N" of first portions to be generated based on the waveform signal 310. It can be said that the pre-determined number "N" of first portions may represent a number of frequency bands from the waveform signal 310 to be shifted towards higher frequencies. For example, the processor 110 may be configured to use one or more filtering operations described above for isolating respective ones of the plurality of N first portions from the waveform signal 310.

Figure 17:
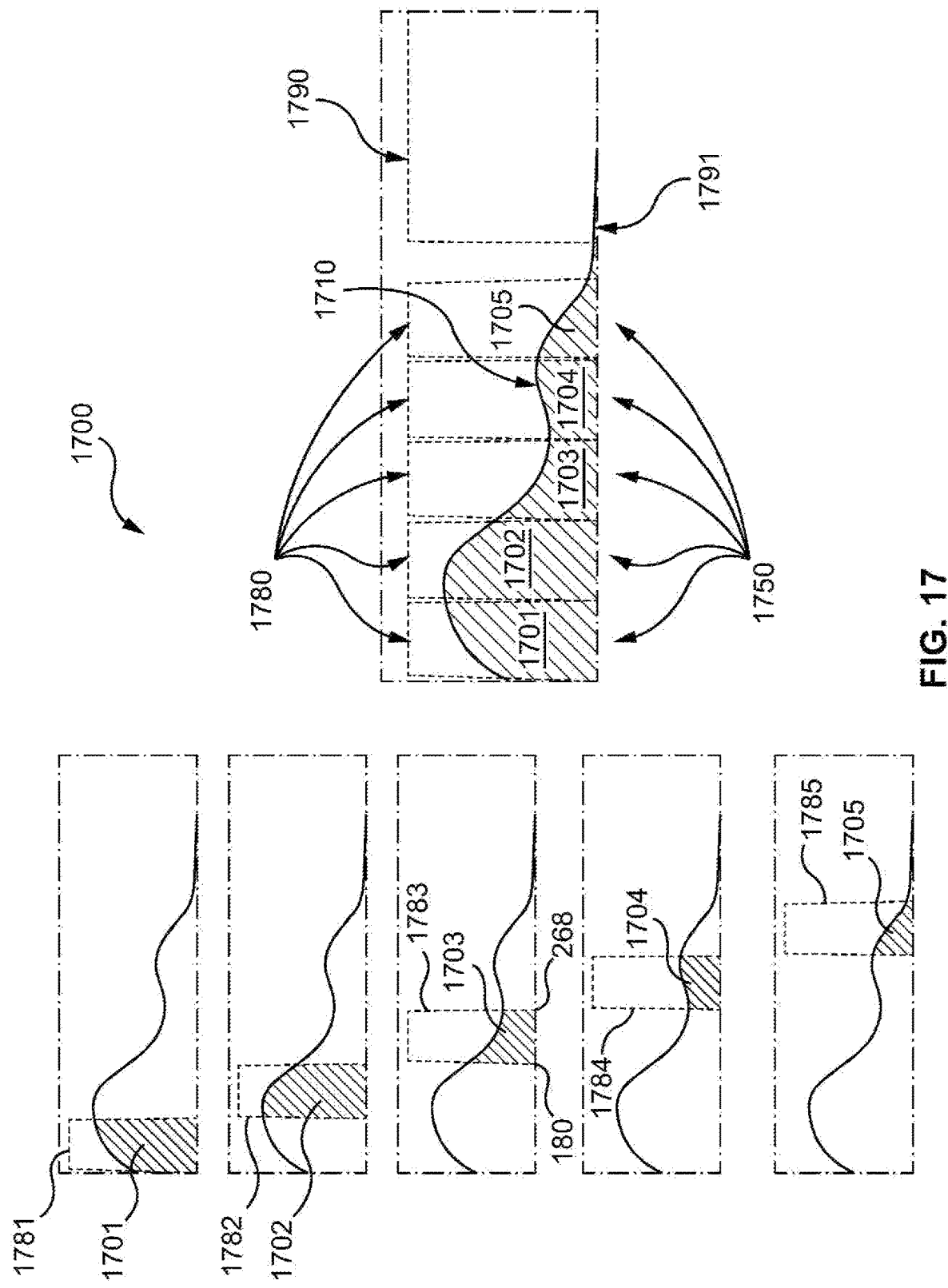
FIG. 17 depicts a representation of how the processor of FIG. 1 is configured to isolate a plurality of first portions from a given waveform signal, in accordance with some non-limiting embodiments of the present technology.

To better illustrate this, reference will now be made to FIG. 17 depicting a representation 1700 of how a plurality of first portions 1750 can be isolated from a given waveform signal. In FIG. 17, there is depicted a frequency spectrum 1710 of the given waveform signal for ease of illustration only, but it should be noted that the processing is performed by the processor 110 in time-domain, as described above, without departing from the scope of the present technology.

Let it be assumed that the given FS value is 45 Hz, the inter-portion value is 2 Hz, and the processor 110 acquires the pre-determined number N of first portions equal to 5 (e.g., N=5). In this example, the processor 110 may be configured to isolate from the given waveform signal the following five first portions by using a plurality of bandpass filters 1780 (which can be implemented as described above):

a first portion 1701 in the 0-88 Hz frequency range, via a first bandpass filter 1781;

a first portion 1702 in the 90-178 Hz frequency range, via a second bandpass filter 1782;

a first portion 1703 in the 180-268 Hz frequency range, via a third bandpass filter 1783;

a first portion 1704 in the 270-358 Hz frequency range, via a fourth bandpass filter 1784; and a first portion 1705 in the 360-448 Hz frequency range, via a fifth bandpass filter 1785.

In at least some embodiments, it can be said that a signal may be filtered by N bandpass filters with cut-off frequencies as expressed in equations (1) and (2) below for generating N intermediate signals, the frequency components of which can be shifted to higher frequencies:

$$Fp1 \cdot n = (n-1)*2*Fs \tag{1}$$

$$Fp2 \cdot n = n*2*Fs - Fdef \tag{2}$$

wherein $Fp1 \cdot n$ and $Fp2 \cdot n$ are cut-off frequency values, and n=1 ... N corresponding to a respective frequency range number.

It should also be noted FIG. 17 also depicts how the processor 110 can apply another filter 1790 to isolate a high-frequency portion 1791 of the given waveform signal, herein sometimes referred to as "$F_h$", for future use thereof. In some embodiments, this high-frequency portion may be defined as $Fh=(N+0.5)*2*Fs$.

It should be noted that each one of the plurality of first portions 1750 may be modulated by the processor 110 similarly to how the first portion of the waveform signal 310 is modulated by the processor 110. It should be noted that the length of the modulating signal is to be equal to the time length of the signal 310. As explained above, such modulation results in a signal comprising a first frequency portion and a second frequency portion (e.g., mirror portion of the resulting modulated signal). As such, the processor 110 may be configured to remove the frequency portion corresponding to the mirror frequency portion from respective modulated signals.

Figure 18:
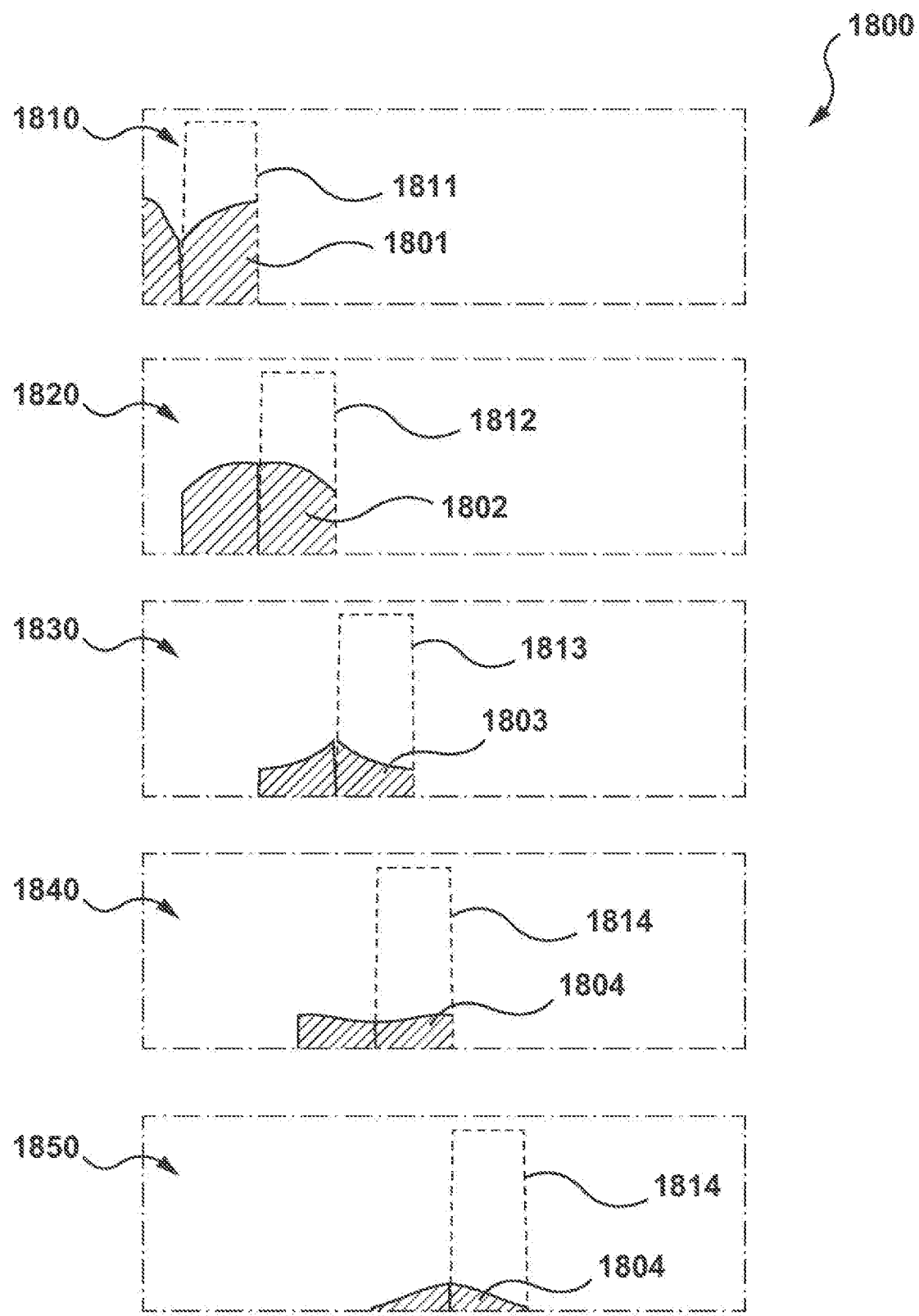
FIG. 18 depicts a representation of how the processor of FIG. 1 is configured to apply bandpass filters for isolating first frequency portions from respective modulated signals, in accordance with some non-limiting embodiments of the present technology.

To better illustrate this, reference will now be made to FIG. 18 depicting a representation 1800 of how the processor 110 may apply bandpass filters for isolating first frequency portions from respective modulated signals generated based on respective first portions from the plurality of first portions 1750. For example, the processor 110 may be configured to apply:

a bandpass filter 1811 (45-133 Hz) on a modulated signal 1810 generated for the first portion 1701, thereby generating a first frequency portion 1801;

a bandpass filter 1812 (135-223 Hz) on a modulated signal 1820 generated for the first portion 1702, thereby generating a first frequency portion 1802;

a bandpass filter 1813 (225-313 Hz) on a modulated signal 1830 generated for the first portion 1703, thereby generating a first frequency portion 1803;

a bandpass filter 1814 (315-403 Hz) on a modulated signal 1840 generated for the first portion 1704, thereby generating a first frequency portion 1804; and a bandpass filter 1815 (405-493 Hz) on a modulated signal 1850 generated for the first portion 1705, thereby generating a first frequency portion 1805.

In at least some embodiments of the present technology, it can be said that band-pass filtering may be performed for removing the carrier frequency and mirror frequencies in the resulting interim signals. This band-pass filters for this operation may be expressed in equations (3) and (4) that follow:

$$Fs1 \cdot n = (n-0.5)*2*Fs, \quad (3)$$

$$Fs2 \cdot n = (n+0.5)*2*Fs - Fdef \quad (4)$$

wherein $Fs1 \cdot n$ and $Fs2 \cdot n$ are cut-off frequency values, and $n=1 \ldots N$ corresponding to a respective frequency range number.

It should be noted that, similarly to what has been described above, processor 110 may be configured to normalize (e.g., amplify) the first frequency portions 1801, 1802, 1803, 1804, and 1805. For example, the processor 110 may increase two-fold the amplitude for the first frequency portions 1801, 1802, 1803, 1804, and 1805.

In some embodiments, the processor 110 may be configured to combine the first frequency portions 1801, 1802, 1803, 1804, and 1805 (and/or the normalized versions thereof) with the high-frequency portion 1791 to generate a given modified waveform signal. With reference to FIG. 19, there is depicted a representation 1900 of a frequency spectrum 1910 of the given modified waveform signal. It can be said that the frequency spectrum 1910 is frequency spectrum 1710 of the given waveform signal that is shifted by the processor 110 towards higher frequencies in accordance with at least some embodiments of the present technology.

It should be expressly understood that not all technical effects mentioned herein need to be enjoyed in each and every embodiment of the present technology. For example, embodiments of the present technology may be implemented without the user enjoying some of these technical effects, while other embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fibre-optic connection), electronic means (such as using wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method of time-domain processing of a waveform signal for generating a modified waveform signal, the waveform signal being representative of bodily sounds, the method executable by a processor, the waveform signal being available to the processor, the method comprising:

filtering, by employing one or more cut-off frequency values, the waveform signal for generating a first portion of the waveform signal and a second portion of the waveform signal, the first portion being in a first frequency range, the second portion being in a frequency range that is inside a human-audible frequency range;

acquiring a frequency shift value indicative of a frequency range by which the first portion is to be shifted to frequencies above the first frequency range;

generating a modulated signal using the first portion and a modulation signal, the modulation signal having a frequency equal to the frequency shift value and a time-length equal to a time-length of the waveform signal, the modulated signal comprising a first frequency portion being in a frequency range that is above the frequency shift value and a second frequency portion being in a frequency range that is below the frequency shift value, the one or more cut-off frequency values having been determined so that the first frequency portion and the second frequency portion are in substantially non-overlapping frequency ranges of the modulated signal, the first frequency portion being a modified representation of the first portion of the waveform signal, the frequency range of the first frequency portion being inside the human-audible frequency range; and generating the modified waveform using the first frequency portion of the modulated signal; and wherein the processor is part of an electronic stethoscope.

2. The method of claim 1, wherein the method further comprises generating the modified waveform signal as a combination of the second portion of the waveform signal and the first frequency portion.

3. The method of claim 1, wherein the one or more cut-off frequency values have been determined for ensuring that the first frequency portion and the second frequency portion are in non-overlapping frequency ranges of the modulated signal.

4. The method of claim 1, wherein the first portion of the waveform signal is a non-audible portion and the second portion is an audible portion of the waveform signal, the non-audible portion being in a frequency range that is outside the human-audible frequency range.

5. The method of claim 1, wherein the method further comprises:

determining the one or more cut-off frequency values based on an input from a human operator.

6. The method of claim 1, wherein the filtering comprises:

filtering, by employing a first and a second cut-off frequency values, the waveform signal for generating the first portion, the second cut-off frequency value depending on the frequency shift value.

7. The method of claim 6, wherein the first cut-off frequency value is 5 Hz and the second cut-off frequency value is 90 Hz.

8. The method of claim 1, wherein the method further comprises:

filtering, by employing a third cut-off frequency value, the modulated signal for generating the first frequency portion, the third cut-off frequency value depending on the first cut-off frequency value and the frequency shift value.

9. The method of claim 8, wherein the third cut-off frequency value is 50 Hz.

10. The method of claim 1, wherein the generating the modified signal comprises:
generating a normalized signal based on the first frequency portion; and
generating the modified signal as a combination of the normalized signal and the second portion.

11. The method of claim 10, wherein the fourth cut-off frequency value is 135 Hz.

12. The method of claim 1, wherein the filtering comprises:
filtering, by employing a fourth cut-off frequency values, the waveform signal for generating the second portion, the fourth cut-off frequency value depending on the frequency shift value.

13. The method of claim 1, wherein the frequency shift value is acquired from a memory associated with the processor.

14. The method of claim 1, wherein the frequency shift value is acquired as an input of a human operator.

15. The method of claim 1, wherein the method further comprises:
storing, in a memory, the modified waveform signal.

16. The method of claim 1, wherein the method further comprises:
triggering generation of sound representative of the modified waveform signal for a human operator.

17. The method of claim 1, wherein the frequency shift value is 45 Hz.

18. The method of claim 1, wherein the waveform signal comprises a plurality of first portions including the first portion, and wherein:
the generating the modulated signal comprises generating a plurality of modulated signals using the respective ones of the plurality of first portions and the modulated signal, the plurality of modulated signals comprising a plurality of first frequency portions, and
the generating the modified waveform signal comprises generating the modified waveform signal as a combination of the second portion of the waveform signal and the plurality of first frequency portions.

19. A processor for time-domain processing of a waveform signal for generating a modified waveform signal, the waveform signal being representative of bodily sounds, the waveform signal being available to the processor, the processor being configured to:
filter, by employing one or more cut-off frequency values, the waveform signal for generating a first portion of the waveform signal and a second portion of the waveform signal, the first portion being in a first frequency range, the second portion being in a frequency range that is inside a human-audible frequency range;
acquire a frequency shift value indicative of a frequency range by which the first portion is to be shifted to frequencies above the first frequency range;
generate a modulated signal using the first portion and a modulation signal, the modulation signal having a frequency equal to the frequency shift value and a time-length equal to a time-length of the waveform signal,
the modulated signal comprising a first frequency portion being in a frequency range that is above the frequency shift value and a second frequency portion being in a frequency range that is below the frequency shift value,
the one or more cut-off frequency values having been determined so that the first frequency portion and the second frequency portion are in substantially non-overlapping frequency ranges of the modulated signal,
the first frequency portion being a modified representation of the first portion of the waveform signal, the frequency range of the first frequency portion being inside the human-audible frequency range; and
generate the modified waveform using the first frequency portion of the modulated signal; and
wherein the processor is part of an electronic stethoscope.

20. An electronic stethoscope comprising at least one processor and memory comprising executable instructions which, when executed by the at least one processor, cause the electronic stethoscope to perform time-domain processing of a waveform signal for generating a modified waveform signal, the waveform signal being representative of bodily sounds, the waveform signal being available to the at least one processor, time-domain processing comprising:
filtering, by employing one or more cut-off frequency values, the waveform signal for generating a first portion of the waveform signal and a second portion of the waveform signal, the first portion being in a first frequency range, the second portion being in a frequency range that is inside a human-audible frequency range;
acquiring a frequency shift value indicative of a frequency range by which the first portion is to be shifted to frequencies above the first frequency range;
generating a modulated signal using the first portion and a modulation signal, the modulation signal having a frequency equal to the frequency shift value and a time-length equal to a time-length of the waveform signal,
the modulated signal comprising a first frequency portion being in a frequency range that is above the frequency shift value and a second frequency portion being in a frequency range that is below the frequency shift value,
the one or more cut-off frequency values having been determined so that the first frequency portion and the second frequency portion are in substantially non-overlapping frequency ranges of the modulated signal,
the first frequency portion being a modified representation of the first portion of the waveform signal, the frequency range of the first frequency portion being inside the human-audible frequency range; and
generating the modified waveform using the first frequency portion of the modulated signal.

\* \* \* \* \*